US008496637B2

(12) United States Patent
Hundorf et al.

(10) Patent No.: US 8,496,637 B2
(45) Date of Patent: Jul. 30, 2013

(54) TRI-FOLDED DISPOSABLE ABSORBENT ARTICLE, PACKAGED ABSORBENT ARTICLE, AND ARRAY OF PACKAGED ABSORBENT ARTICLES WITH SUBSTANTIALLY CONTINUOUSLY DISTRIBUTED ABSORBENT PARTICULATE POLYMER MATERIAL

(75) Inventors: Harald Hermann Hundorf, Bonn (DE);
Holger Beruda, Schwalbach (DE);
Horst Blessing, Cincinnati, OH (US);
Peter Dziezok, Hochheim (DE); Axel Krause, Erftstadt (DE); Mattias Schmidt, Idstein (DE); Lutz Stelzig, Frankfurt am Main (DE); Martin Werner Frank, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 681 days.

(21) Appl. No.: 12/141,146

(22) Filed: Jun. 18, 2008

(65) Prior Publication Data
US 2008/0312624 A1 Dec. 18, 2008

Related U.S. Application Data

(60) Provisional application No. 60/936,037, filed on Jun. 18, 2007.

(51) Int. Cl.
*A61F 13/15* (2006.01)
(52) U.S. Cl.
USPC ............... 604/385.02; 604/368; 604/385.201

(58) Field of Classification Search
USPC ............ 604/367–368, 372, 381–382, 385.02, 604/385.201
See application file for complete search history.

(56) References Cited

U.S. PATENT DOCUMENTS

| | | |
|---|---|---|
| 3,670,731 A | 6/1972 | Harmon |
| 3,848,594 A | 11/1974 | Buell |
| 3,860,003 A | 1/1975 | Buell |
| 4,055,180 A | 10/1977 | Karami |
| 4,259,220 A | 3/1981 | Bunnelle et al. |
| 4,381,783 A | 5/1983 | Elias |
| 4,469,710 A | 9/1984 | Rielley et al. |
| 4,515,595 A | 5/1985 | Kievie |
| 4,596,568 A | 6/1986 | Flug |
| 4,610,678 A | 9/1986 | Weisman et al. |

(Continued)

FOREIGN PATENT DOCUMENTS

| | | |
|---|---|---|
| EP | 0 149 880 A2 | 7/1985 |
| EP | 0 203 289 A2 | 12/1986 |

(Continued)

OTHER PUBLICATIONS

International Search Report, mailed Nov. 21, 2008, PCT/IB2008/052350.

*Primary Examiner* — Lynne Anderson
(74) *Attorney, Agent, or Firm* — Christian M. Best; Laura L. Whitmer; John P. Colbert

(57) ABSTRACT

A tri-folded disposable absorbent article comprising a substantially cellulose free absorbent core located in a chassis between a topsheet and a backsheet and comprising absorbent particulate polymer material. An array of absorbent article packages comprising disposable absorbent articles comprising a substantially cellulose free absorbent core is also disclosed.

10 Claims, 16 Drawing Sheets

U.S. PATENT DOCUMENTS

| | | |
|---|---|---|
| 4,662,875 A | 5/1987 | Hirotsu et al. |
| 4,670,011 A | 6/1987 | Mesek |
| 4,695,278 A | 9/1987 | Lawson |
| 4,704,115 A | 11/1987 | Buell |
| RE32,649 E | 4/1988 | Brandt et al. |
| 4,834,735 A | 5/1989 | Alemany et al. |
| 4,848,815 A | 7/1989 | Molloy |
| 4,869,724 A | 9/1989 | Scripps |
| 4,888,231 A | 12/1989 | Angstadt |
| 4,909,803 A | 3/1990 | Aziz et al. |
| 4,940,464 A | 7/1990 | Van Gompel et al. |
| 4,960,477 A | 10/1990 | Mesek |
| 4,994,053 A | 2/1991 | Lang |
| 5,032,120 A | 7/1991 | Freeland et al. |
| 5,037,416 A | 8/1991 | Allen et al. |
| 5,087,255 A | 2/1992 | Sims et al. |
| 5,092,861 A | 3/1992 | Nomura et al. |
| 5,124,188 A | 6/1992 | Roe et al. |
| 5,137,537 A | 8/1992 | Herron et al. |
| 5,143,679 A | 9/1992 | Weber et al. |
| 5,151,092 A | 9/1992 | Buell et al. |
| 5,156,793 A | 10/1992 | Buell et al. |
| 5,167,897 A | 12/1992 | Weber et al. |
| 5,242,436 A | 9/1993 | Weil et al. |
| 5,246,433 A | 9/1993 | Hasse et al. |
| 5,260,345 A | 11/1993 | DesMarais et al. |
| 5,269,775 A | 12/1993 | Freeland et al. |
| 5,387,207 A | 2/1995 | Dyer et al. |
| 5,397,316 A | 3/1995 | LaVon et al. |
| 5,401,792 A | 3/1995 | Babu et al. |
| 5,411,497 A | 5/1995 | Tanzer et al. |
| 5,425,725 A | 6/1995 | Tanzer et al. |
| 5,460,622 A | 10/1995 | Dragoo et al. |
| 5,518,801 A | 5/1996 | Chappell et al. |
| 5,527,300 A | 6/1996 | Sauer |
| 5,554,145 A | 9/1996 | Roe et al. |
| 5,562,646 A | 10/1996 | Goldman et al. |
| 5,569,234 A | 10/1996 | Buell et al. |
| 5,571,096 A | 11/1996 | Dobrin et al. |
| 5,591,155 A | 1/1997 | Nishikawa et al. |
| 5,599,335 A | 2/1997 | Goldman et al. |
| 5,625,222 A | 4/1997 | Yoneda et al. |
| 5,628,741 A | 5/1997 | Buell et al. |
| 5,658,268 A | 8/1997 | Johns et al. |
| 5,762,641 A | 6/1998 | Bewick-Sonntag et al. |
| 5,788,684 A | 8/1998 | Abuto et al. |
| 5,833,678 A | 11/1998 | Ashton et al. |
| 5,897,545 A | 4/1999 | Kline et al. |
| 5,944,706 A | 8/1999 | Palumbo et al. |
| 5,957,908 A | 9/1999 | Kline et al. |
| 6,004,306 A | 12/1999 | Robles et al. |
| 6,090,994 A | 7/2000 | Chen |
| 6,120,487 A | 9/2000 | Ashton |
| 6,120,489 A | 9/2000 | Johnson et al. |
| 6,132,411 A | 10/2000 | Huber et al. |
| 6,231,556 B1 | 5/2001 | Osborn, III |
| 6,258,996 B1 | 7/2001 | Goldman |
| 6,368,687 B1 | 4/2002 | Joseph et al. |
| 6,376,034 B1 | 4/2002 | Brander |
| 6,383,431 B1 | 5/2002 | Dobrin et al. |
| 6,429,350 B1 | 8/2002 | Tanzer et al. |
| 6,458,877 B1 | 10/2002 | Ahmed et al. |
| 6,645,569 B2 | 11/2003 | Cramer et al. |
| 6,705,465 B2 | 3/2004 | Ling et al. |
| 6,863,933 B2 | 3/2005 | Cramer et al. |
| 6,972,011 B2 | 12/2005 | Maeda et al. |
| 7,108,916 B2 | 9/2006 | Ehrnsperger et al. |
| 7,112,621 B2 | 9/2006 | Rohrbaugh et al. |
| 7,237,370 B1 * | 7/2007 | Garone et al. ............ 53/429 |
| 2002/0007169 A1 | 1/2002 | Graef et al. |
| 2002/0102392 A1 | 8/2002 | Fish et al. |
| 2002/0115969 A1 | 8/2002 | Maeda et al. |
| 2002/0151634 A1 | 10/2002 | Rohrbaugh et al. |
| 2002/0192366 A1 | 12/2002 | Cramer et al. |
| 2003/0105190 A1 | 6/2003 | Diehl et al. |
| 2003/0148684 A1 | 8/2003 | Cramer et al. |
| 2003/0233082 A1 | 12/2003 | Kline et al. |
| 2004/0097895 A1 | 5/2004 | Busam et al. |
| 2004/0097897 A1 * | 5/2004 | Ronn et al. ............ 604/385.02 |
| 2004/0158212 A1 | 8/2004 | Ponomarenko et al. |
| 2004/0162536 A1 | 8/2004 | Becker et al. |
| 2004/0167486 A1 * | 8/2004 | Busam et al. ............ 604/367 |
| 2004/0167489 A1 | 8/2004 | Kellenberger et al. |
| 2005/0008839 A1 | 1/2005 | Cramer et al. |
| 2005/0131371 A1 * | 6/2005 | Fell et al. ............ 604/385.02 |
| 2005/0159720 A1 | 7/2005 | Gentilcore et al. |
| 2005/0229543 A1 | 10/2005 | Tippey |
| 2006/0069372 A1 * | 3/2006 | Chakravarty et al. .... 604/385.02 |
| 2006/0177647 A1 | 8/2006 | Schmidt et al. |
| 2006/0206083 A1 * | 9/2006 | Corlett ............ 604/385.02 |
| 2006/0240229 A1 | 10/2006 | Erhnsperger et al. |
| 2007/0043330 A1 | 2/2007 | Lankhof et al. |
| 2007/0088308 A1 | 4/2007 | Ehrnsperger et al. |
| 2007/0118087 A1 | 5/2007 | Flohr et al. |
| 2007/0156108 A1 | 7/2007 | Becker et al. |
| 2007/0167928 A1 | 7/2007 | Becker et al. |
| 2007/0179464 A1 | 8/2007 | Becker et al. |
| 2007/0219521 A1 | 9/2007 | Hird et al. |
| 2008/0051749 A1 * | 2/2008 | Betts et al. ............ 604/385.02 |
| 2008/0082071 A1 * | 4/2008 | Bryant et al. ............ 604/385.02 |

FOREIGN PATENT DOCUMENTS

| | | |
|---|---|---|
| EP | 0 640 330 A1 | 3/1995 |
| EP | 1 088 537 A2 | 4/2001 |
| EP | 1 447 067 A | 8/2004 |
| EP | 1621167 | 2/2006 |
| JP | 06-269475 | 9/1994 |
| JP | 2002-113800 | 4/2002 |
| JP | 2002-325799 | 11/2002 |
| WO | WO 95/16746 A1 | 6/1995 |
| WO | WO 97/11659 | 4/1997 |
| WO | WO 01/15647 | 3/2001 |
| WO | WO 02/064877 A2 | 8/2002 |
| WO | WO 2004/071539 A3 | 8/2004 |
| WO | WO 2006/062258 A2 | 6/2006 |

* cited by examiner

TRI-FOLDED DISPOSABLE ABSORBENT ARTICLE, PACKAGED ABSORBENT ARTICLE, AND ARRAY OF PACKAGED ABSORBENT ARTICLES WITH SUBSTANTIALLY CONTINUOUSLY DISTRIBUTED ABSORBENT PARTICULATE POLYMER MATERIAL

CROSS REFERENCE TO RELATED APPLICATIONS

This application claims the benefit of U.S. Provisional Application No. 60/936,037, filed on Jun. 18, 2007.

FIELD OF THE INVENTION

The present invention generally relates to an absorbent article, and more particularly to packaging and display of disposable absorbent articles.

BACKGROUND OF THE INVENTION

Absorbent articles, such as disposable diapers, training pants, and adult incontinence undergarments, absorb and contain body exudates. They also are intended to prevent body exudates from soiling, wetting, or otherwise contaminating clothing or other articles, such as bedding, that come in contact with the wearer.

Disposable absorbent articles are often purchased and used in a relatively large volume. Disposable diapers, for example, may be packaged in packages containing multiple diapers, often about 20 to about 40 diapers or more in a single package. Although absorbent articles, such as diapers, may be somewhat bulky, they have been made thinner largely due to use of absorbent polymer materials (also known as superabsorbent polymers). Absorbent polymer material allows disposable absorbent articles to be made relatively thin and flexible, but they may still occupy a relatively large volume of space during shipping, storage, and/or retail shelf display.

The space occupied by disposable absorbent articles affects the ability to transport, store, and/or display absorbent articles efficiently and conveniently. The greater the space occupied by absorbent articles, the higher the cost of providing such products to the end consumer. The space occupied by absorbent articles may also be an inconvenience for the end user as well, particularly if transportation or storage space available for the absorbent articles is relatively small.

The shape of absorbent articles, such as diapers, also affects the ability to transport, store, and/or display absorbent articles cost efficiently and conveniently. The shape of absorbent article packaging may be limited by the shape of the absorbent article. Absorbent articles, such as diapers, typically are longer than wide and therefore the packaging for such articles tends to follow the same shape. Disposable diapers for example, may be folded, such as in a bi-fold configuration and stacked for packaging in a packaging material such as a bag, pouch, box, or the like. Even when folded, diapers tend to be longer than wide. Some diapers are too thick for multiple folds or are damaged by multiple folding of the diaper. Thus, the packaging configurations available for absorbent articles are limited and available transportation, storage, and/or retail display space may not be configured well for efficient and convenient transportation, storage, and/or display of packaged absorbent articles.

Thus, there remains a need for absorbent articles, such as diapers, that may be packaged in configurations that may be more efficient or convenient for transportation, storage, and/or display.

SUMMARY OF THE INVENTION

The present invention addresses one or more technical problems described above and provides a tri-folded disposable absorbent article comprising a chassis including a liquid permeable topsheet and a liquid impermeable backsheet and a substantially cellulose free absorbent core located between the topsheet and the backsheet and comprising absorbent particulate polymer material. The disposable absorbent article has a longitudinal axis extending from a first end to a second end and is folded substantially perpendicularly to the longitudinal axis along a first fold line and a second fold line spaced from the first fold line so as to form a central section extending from the first fold line to the second fold line, a first end section extending from the first fold line to the first end, and a second end section extending from the second fold line to the second end, so that the first section, central section, and second section are superposed to one another.

According to another aspect of this invention, an array of absorbent article packages is provided and comprises a plurality of absorbent article packages, each of the absorbent article packages comprising a packaging material and a plurality of disposable absorbent articles disposed in the packaging material in a substantially superposed stacked configuration. The disposable absorbent articles each comprise a chassis including a liquid permeable topsheet and a liquid impermeable backsheet and a substantially cellulose free absorbent core located between the topsheet and the backsheet. The absorbent core comprises absorbent particulate polymer material. Further, at least a first of the plurality of absorbent article packages comprise disposable absorbent articles having a first size and occupying a volume in the at least first of the plurality of absorbent article packages of less than about 200 cc per absorbent article and at least a second of the plurality of absorbent article packages comprise disposable absorbent articles having a second size different than the first size and occupying a volume in the at least a second of the plurality of absorbent article packages different than the volume occupied by the disposable absorbent articles having the first size in the first of the plurality of absorbent article packages.

Other features and advantages of the invention may be apparent from reading the following detailed description, drawings, and claims.

BRIEF DESCRIPTION OF THE DRAWINGS

FIG. 15A is a perspective view of the diaper illustrated in FIG. 1 with sides folded in.

FIG. 15B is a perspective view of the diaper illustrated in FIG. 1 with sides and one end folded in.

DETAILED DESCRIPTION OF THE INVENTION

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic composition, and optionally the cover layer.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

Figure 8:
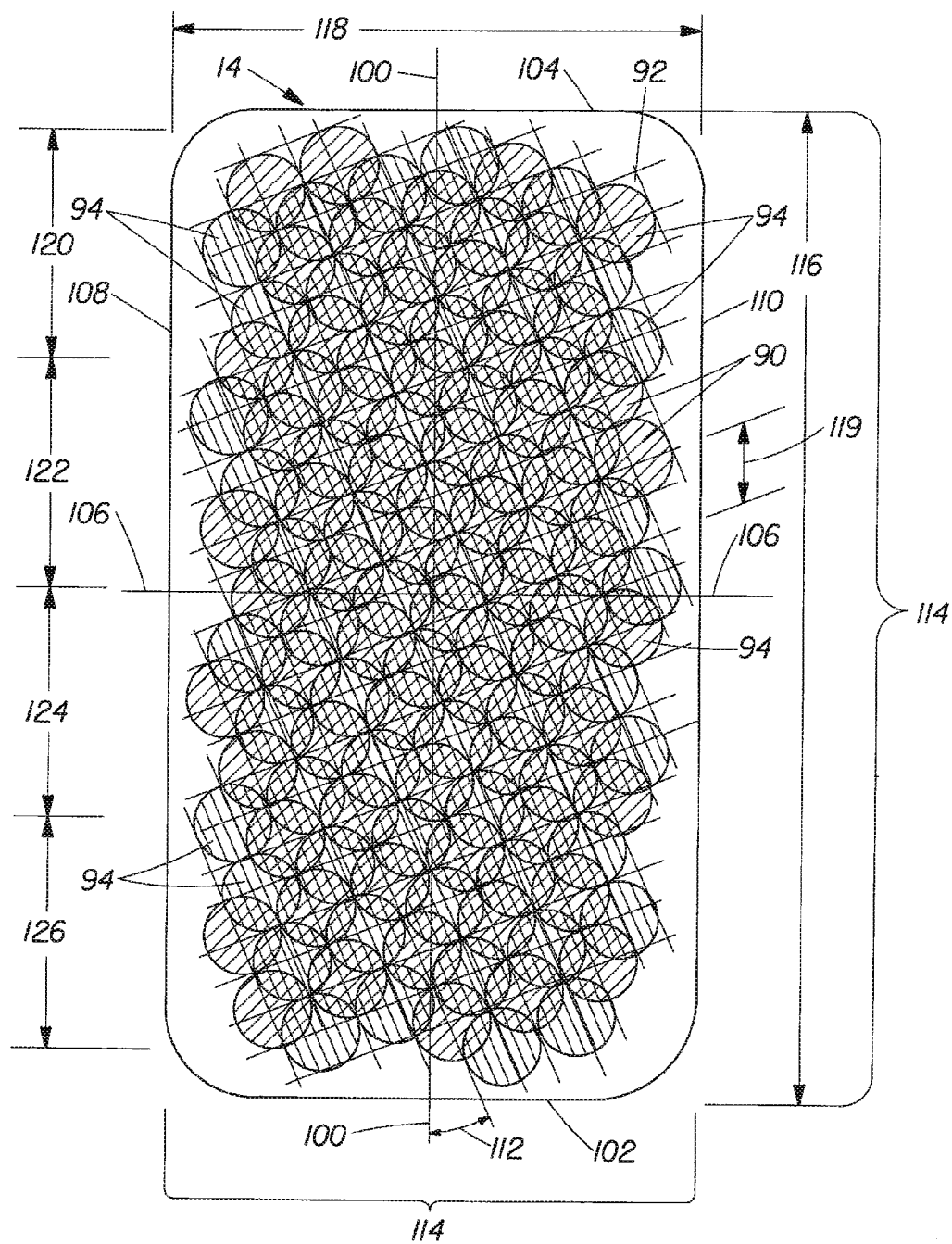
FIG. 8 is a plan view of the absorbent core illustrated in FIGS. 7a and 7b.

"Absorbent particulate polymer material area" as used herein refers to the area of the core wherein the first substrate 64 and second substrate 72 are separated by a multiplicity of superabsorbent particles. In FIG. 8, the boundary of the absorbent particulate polymer material area is defined by the perimeter of the overlapping circles. There may be some extraneous superabsorbent particles outside of this perimeter between the first substrate 64 and second substrate 72.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present invention forms a fibrous network over the superabsorbent material.

"Thickness" and "caliper" are used herein interchangeably.

Figure 1:
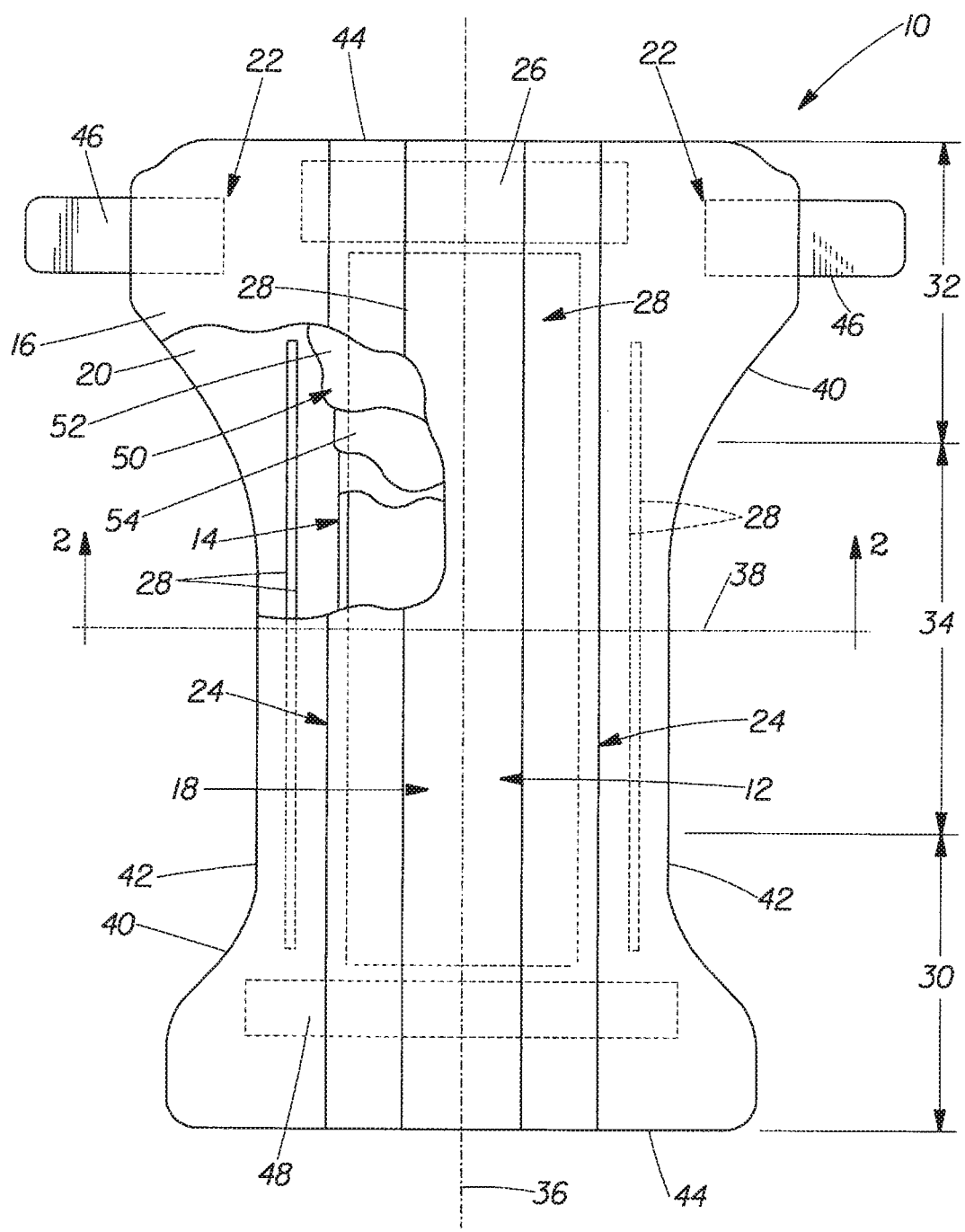
FIG. 1 is a plan view of a diaper in accordance with an embodiment of the present invention.

FIG. 1 is a plan view of a diaper 10 according to a certain embodiment of the present invention. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 20 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

According to certain embodiments, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 may be joined with the topsheet 18. The backsheet 20 may prevent the exudates absorbed by the absorbent core 14 and contained within the diaper 10 from soiling other external articles that may contact the diaper 10, such as bed sheets and undergarments. In certain embodiments, the backsheet 26 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

In certain embodiments, the backsheet of the present invention may have a water vapor transmission rate (WVTR) of greater than about 2000 g/24 h/m$^2$, greater than about 3000 g/24 h/m$^2$, greater than about 5000 g/24 h/m$^2$, greater than about 6000 g/24 h/m$^2$, greater than about 7000 g/24 h/m$^2$, greater than about 8000 g/24 h/m$^2$, greater than about 9000 g/24 h/m$^2$, greater than about 10000 g/24 h/m$^2$, greater than about 11000 g/24 h/m$^2$, greater than about 12000 g/24 h/m$^2$, greater than about 15000 g/24 h/m$^2$, measured according to WSP 70.5 (08) at 37.8° C. and 60% Relative Humidity.

Figure 2:
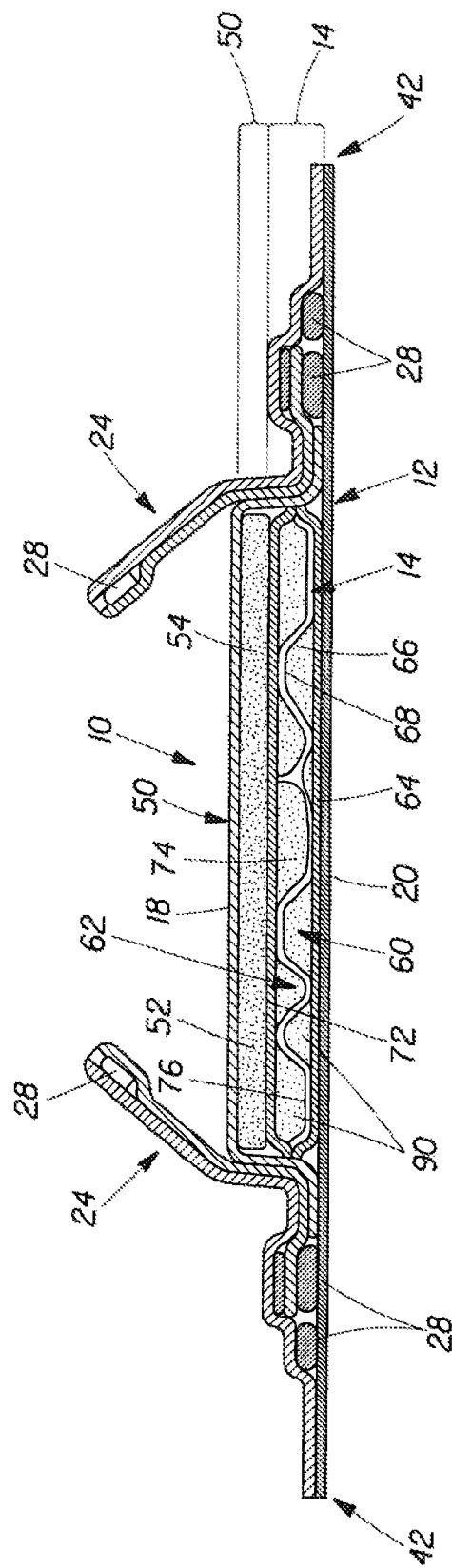
FIG. 2 is a cross sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side, the diaper 10 may comprise the topsheet 18, the components of the absorbent core 14, and the backsheet 20. According to a certain embodiment, diaper 10 may also comprise an acquisition system 50 disposed between the liquid permeable topsheet 18 and a wearer facing side of the absorbent core 14. The acquisition system 50 may be in direct contact with the absorbent core. The acquisition system 50 may comprise a single layer or multiple layers, such as an upper acquisition layer 52 facing towards the wearer's skin and a lower acquisition 54 layer facing the garment of the wearer. According to a certain embodiment, the acquisition system 50 may function to receive a surge of liquid, such as a gush of urine. In other words, the acquisition system 50 may serve as a temporary reservoir for liquid until the absorbent core 14 can absorb the liquid.

In a certain embodiment, the acquisition system 50 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers 52 and 54 may comprise a non-woven, which may be hydrophilic. Further, according to a certain embodiment, one or both of the upper and lower acquisition layers 52 and 54 may comprise the chemically cross-linked cellulosic fibers, which may or may not form part of a nonwoven material. According to an exemplary embodiment, the upper acquisition layer 52 may comprise a nonwoven, without the cross-linked cellulosic fibers, and the lower acquisition layer 54 may comprise the chemically cross-linked cellulosic fibers. Further, according to an embodiment, the lower acquisition layer 54 may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. According to a particular embodiment, the lower acquisition layer 54 has a total dry weight, the cross-linked cellulosic fibers are present on a dry weight basis in the upper acquisition layer in an amount from about 30% to about 95% by weight of the lower acquisition layer 54, and the other natural or synthetic polymeric fibers are present on a dry weight basis in the lower acquisition layer 54 in an amount from about 70% to about 5% by weight of the lower acquisition layer 54. According to another embodiment, the cross-linked cellulosic fibers are present on a dry weight basis in the first acquisition layer in an amount from about 80% to about 90% by weight of the lower acquisition layer 54, and the other natural or synthetic polymeric fibers are present on a dry weight basis in the lower acquisition layer 54 in an amount from about 20% to about 10% by weight of the lower acquisition layer 54.

According to a certain embodiment, the lower acquisition layer 54 desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. According to exemplary embodiments, the lower acquisition layer 54 has a maximum uptake of about 10 g/g.

A relevant attribute of the upper acquisition layer 54 is its Median Desorption Pressure, MDP. The MDP is a measure of the capillary pressure that is required to dewater the lower acquisition layer 54 to about 50% of its capacity at 0 cm capillary suction height under an applied mechanical pressure of 0.3 psi. Generally, a relatively lower MDP may be useful. The lower MDP may allow the lower acquisition layer 54 to more efficiently drain the upper acquisition material. Without wishing to be bound by theory, a given distribution material may have a definable capillary suction. The ability of the lower acquisition layer 54 to move liquid vertically via capillary forces will be directly impacted by gravity and the opposing capillary forces associated with desorption of the upper acquisition layer. Minimizing these capillary forces may positively impact the performance of the lower acquisition layer 54. However, in a certain embodiment the lower acquisition layer 54 may also have adequate capillary absorption suction in order to drain the layers above (upper acquisition layer 52 and topsheet 18, in particular) and to temporarily hold liquid until the liquid can be partitioned away by the absorbent core components. Therefore, in a certain embodiment, the lower acquisition layer 54 may have a minimum MDP of greater than 5 cm. Further, according to exemplary embodiments, the lower acquisition layer 54 has an MDP value of less than about 20.5 cm $H_2O$, or less than about 19 cm $H_2O$, or less than about 18 cm $H_2O$ to provide for fast acquisition.

The methods for determining MDP and maximum uptake are disclosed in U.S. patent application Ser. No. 11/600,691 (Flohr et al.). For example, according to a first embodiment, the lower acquisition layer 54 may comprise about 70% by weight of chemically cross-linked cellulose fibers, about 10% by weight polyester (PET), and about 20% by weight untreated pulp fibers. According to a second embodiment, the lower acquisition layer 54 may comprise about 70% by weight chemically cross-linked cellulose fibers, about 20% by weight lyocell fibers, and about 10% by weight PET fibers. According to a third embodiment, the lower acquisition layer 54 may comprise about 68% by weight chemically cross-linked cellulose fibers, about 16% by weight untreated pulp fibers, and about 16% by weight PET fibers. In one embodiment, the lower acquisition layer 54 may comprise from about 90-100% by weight chemically cross-linked cellulose fibers.

Suitable non-woven materials for the upper and lower acquisition layers 52 and 54 include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the non-wovens are porous.

In certain embodiments, suitable non-woven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in co-pending applications U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated non-woven is that disclosed in the co-pending patent application Ser. No. 10/758,066 entitled "Disposable absorbent article comprising a durable hydrophilic core wrap" to Ekaterina Anatolyevna Ponomarenko and Mattias NMN Schmidt.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co-pending patent application Ser. Nos. 10/338,603 to Cramer et al. and 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and absorbent core layers comprising permanently hydrophilic non-wovens as described above have been found to work well.

According to a certain embodiment, the upper acquisition layer 52 may comprise a material that provides good recovery when external pressure is applied and removed. Further, according to a certain embodiment, the upper acquisition layer 52 may comprise a blend of different fibers selected, for example from the types of polymeric fibers described above. In some: embodiments, at least a portion of the fibers may exhibit a spiral-crimp which has a helical shape. In some embodiments, the upper acquisition layer 52 may comprise fibers having different degrees or types of crimping, or both. For example, one embodiment may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to a certain embodiment, the fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer 52 may be stabilized by a latex binder, for example a styrene-butadiene latex binder (SB latex), in a certain embodiment. Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

Figure 3:
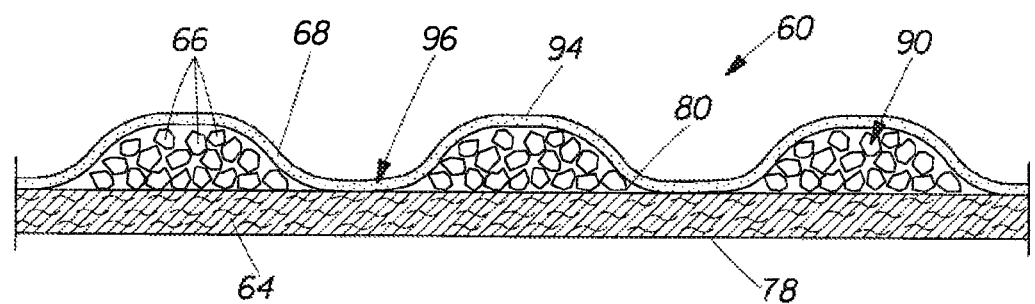
FIG. 3 is a partial cross sectional view of an absorbent core layer in accordance with an embodiment of this invention.

The absorbent core 14 in FIGS. 1-8 generally is disposed between the topsheet 18 and the backsheet 20 and comprises two layers, a first absorbent layer 60 and a second absorbent layer 62. As best shown in FIG. 3, the first absorbent layer 60 of the absorbent core 14 comprises a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic composition 68.

Likewise, as best illustrated in FIG. 2, the second absorbent layer 62 of the absorbent core 14 may also include a substrate 72, an absorbent particulate polymer material 74 on the second substrate 72, and a thermoplastic composition 66 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the backsheet 20 of the diaper 10 and a second surface 80 which faces the absorbent particulate polymer material 66. Likewise, the substrate 72 of the second absorbent layer 62 may be referred to as a core cover and has a first surface 82 facing the topsheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

According to a certain embodiment, the substrates 64 and 72 of the first and second absorbent layers 60 and 62 may be a non-woven material, such as those nonwoven materials described above. In certain embodiments, the non-wovens are porous and in one embodiment has a pore size of about 32 microns.

As illustrated in FIGS. 1-8, the absorbent particulate polymer material 66 and 74 is deposited on the respective substrates 64 and 72 of the first and second absorbent layers 60 and 62 in clusters 90 of particles to form a grid pattern 92 comprising land areas 94 and junction areas 96 between the land areas 94. As defined herein, land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern 92 contain little or no absorbent particulate polymer material 66 and 74. The land areas 94 and junction areas 96 can have a variety of shapes including, but not limited to, circular, oval, square, rectangular, triangular, and the like.

The grid pattern shown in FIG. 8 is a square grid with regular spacing and size of the land areas. Other grid patterns including hexagonal, rhombic, orthorhombic, parallelogram, triangular, rectangular, and combinations thereof may also be used. The spacing between the grid lines may be regular or irregular.

The size of the land areas 94 in the grid patterns 92 may vary. According to certain embodiments, the width 119 of the land areas 94 in the grid patterns 92 ranges from about 8 mm to about 12 mm. In a certain embodiment, the width of the land areas 94 is about 10 mm. The junction areas 96, on the other hand, in certain embodiments, have a width or larger span of less than about 5 mm, less than about 3 mm, less than about 2 mm, less than about 1.5 mm, less than about 1 mm, or less than about 0.5 mm.

As shown in FIG. 8, the absorbent core 14 has a longitudinal axis 100 extending from a rear end 102 to a front end 104 and a transverse axis 106 perpendicular to the longitudinal axis 100 extending from a first edge 108 to a second edge 110. The grid pattern 92 of absorbent particulate polymer material clusters 90 is arranged on the substrates 64 and 72 of the respective absorbent layers 60 and 62 such that the grid pattern 92 formed by the arrangement of land areas 94 and junction areas 96 forms a pattern angle 112. The pattern angle 112 may be 0, greater than 0, or 15 to 30 degrees, or from about 5 to about 85 degrees, or from about 10 to about 60 degrees, or from about 15 to about 30 degrees.

Figure 7A:
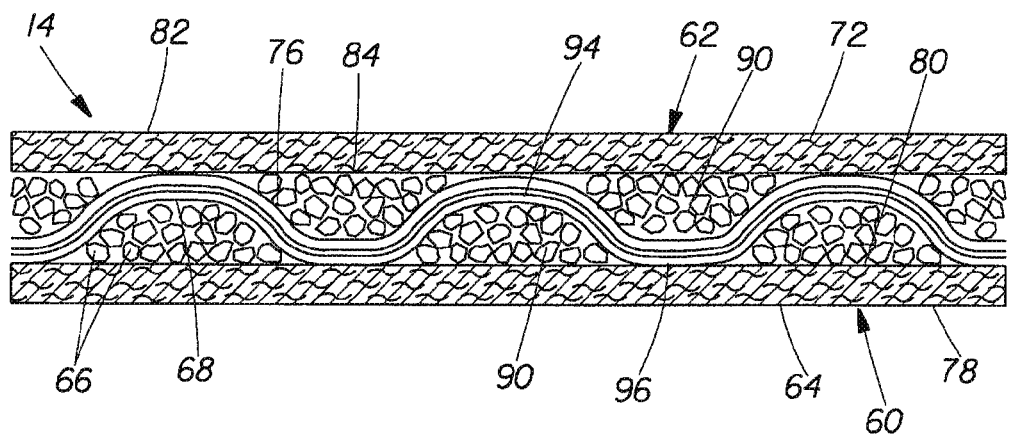
FIG. 7a is a partial sectional view of an absorbent core comprising a combination of the first and second absorbent core layers illustrated in FIGS. 5 and 6.
Figure 7B:
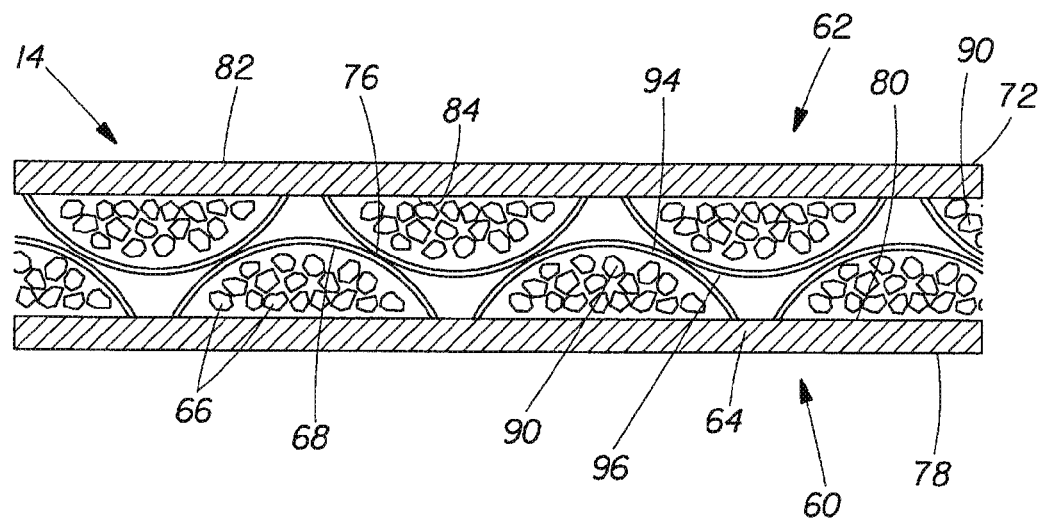
FIG. 7b is a partial sectional view of an absorbent core comprising a combination of the first and second absorbent core layers illustrated in FIGS. 5 and 6

As best seen in FIGS. 7a, 7b, and 8, the first and second layers 60 and 62 may be combined to form the absorbent core 14. The absorbent core 14 has an absorbent particulate polymer material area 114 bounded by a pattern length 116 and a pattern width 118. The extent and shape of the absorbent particulate polymer material area 114 may vary depending on the desired application of the absorbent core 14 and the particular absorbent article in which it may be incorporated. In a certain embodiment, however, the absorbent particulate polymer material area 114 extends substantially entirely across the absorbent core 14, such as is illustrated in FIG. 8.

The first and second absorbent layers 60 and 62 may be combined together to form the absorbent core 14 such that the grid patterns 92 of the respective first and second absorbent layers 62 and 64 are offset from one another along the length and/or width of the absorbent core 14. The respective grid patterns 92 may be offset such that the absorbent particulate polymer material 66 and 74 is substantially continuously distributed across the absorbent particulate polymer area 114. In a certain embodiment, absorbent particulate polymer material 66 and 74 is substantially continuously distributed across the absorbent particulate polymer material area 114 despite the individual grid patterns 92 comprising absorbent particulate polymer material 66 and 74 discontinuously distributed across the first and second substrates 64 and 72 in clusters 90. In a certain embodiment, the grid patterns may be offset such that the land areas 94 of the first absorbent layer 60 face the junction areas 96 of the second absorbent layer 62 and the land areas of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area 114 of the absorbent core 14 (i.e. first and second substrates 64 and 72 do not form a plurality of pockets, each containing a cluster 90 of absorbent particulate polymer material 66 therebetween). In a certain embodiment, respective grid patterns 92 of the first and second absorbent layer 60 and 62 may be substantially the same.

In a certain embodiment as illustrated in FIG. 8, the amount of absorbent particulate polymer material 66 and 74 may vary along the length 116 of the grid pattern 92. In a certain embodiment, the grid pattern may be divided into absorbent zones 120, 122, 124, and 126, in which the amount of absorbent particulate polymer material 66 and 74 varies from zone to zone. As used herein, "absorbent zone" refers to a region of the absorbent particulate polymer material area having boundaries that are perpendicular to the longitudinal axis shown in FIG. 8. The amount of absorbent particulate polymer material 66 and 74 may, in a certain embodiment, gradually transition from one of the plurality of absorbent zones 120, 122, 124, and 126 to another. This gradual transition in amount of absorbent particulate polymer material 66 and 74 may reduce the possibility of cracks forming in the absorbent core 14.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 14 consists essentially of the first and second substrates 64 and 72, the absorbent particulate polymer material 66 and 74, and the thermoplastic adhesive composition 68 and 76. In an embodiment, the absorbent core 14 may be substantially cellulose free.

According to certain embodiments, the weight of absorbent particulate polymer material 66 and 74 in at least one freely selected first square measuring 1 cm×1 cm may be at least about 10%, or 20%, or 30%, 40% or 50% higher than the weight of absorbent particulate polymer material 66 and 74 in at least one freely selected second square measuring 1 cm×1 cm. In a certain embodiment, the first and the second square are centered about the longitudinal axis.

The absorbent particulate polymer material area, according to an exemplary embodiment, may have a relatively narrow width in the crotch area of the absorbent article for increased wearing comfort. Hence, the absorbent particulate polymer material area, according to an embodiment, may have a width as measured along a transverse line which is positioned at equal distance to the front edge and the rear edge of the absorbent article, which is less than about 100 mm, 90 mm, 80 mm, 70 mm, 60 mm or even less than about 50 mm.

It has been found that, for most absorbent articles such as diapers, the liquid discharge occurs predominately in the front half of the diaper. The front half of the absorbent core 14 should therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

Figure 4:
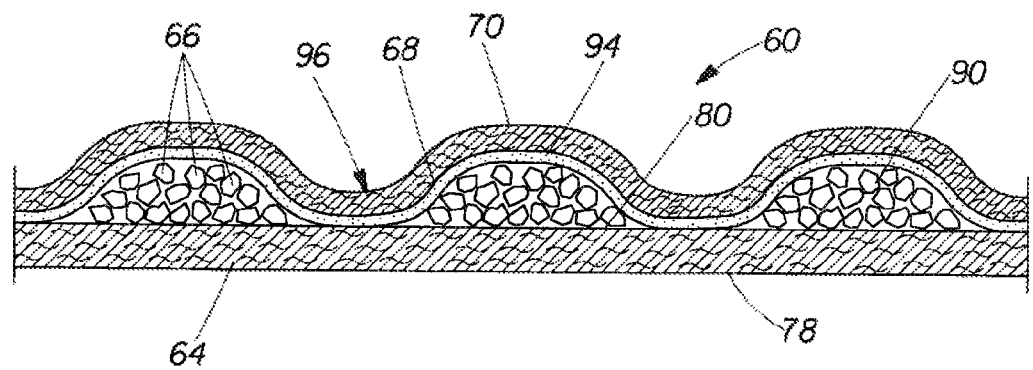
FIG. 4 is a partial cross sectional view of an absorbent core layer in accordance with another embodiment of this invention.

The thermoplastic adhesive material 68 and 76 may serve to cover and at least partially immobilize the absorbent particulate polymer material 66 and 74. In one embodiment of the present invention, the thermoplastic adhesive material 68 and 76 can be disposed essentially uniformly within the absorbent particulate polymer material 66 and 74, between the polymers. However, in a certain embodiment, the thermoplastic adhesive material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3, 4, and 7 show such a structure, and in that structure, the absorbent particulate polymer material 66 and 74 is provided as a discontinuous layer, and a layer of fibrous thermoplastic adhesive material 68 and 76 is laid down onto the layer of absorbent particulate polymer material 66 and 74, such that the thermoplastic adhesive material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent particulate polymer material 68 and 76 and the second surfaces of the substrates 64 and 72.

Thereby, the thermoplastic adhesive material 68 and 76 may provide cavities to cover the absorbent particulate polymer material 66 and 74, and thereby immobilizes this material. In a further aspect, the thermoplastic adhesive material 68 and 76 bonds to the substrates 64 and 72 and thus affixes the absorbent particulate polymer material 66 and 74 to the substrates 64 and 72. Thus, in accordance with certain embodiments, the thermoplastic adhesive material 68 and 76 immobilizes the absorbent particulate polymer material 66 and 74 when wet, such that the absorbent core 14 achieves an absorbent particulate polymer material loss of no more than about 70%, 60%, 50%, 40%, 30%, 20%, 10% according to the Wet Immobilization Test described herein. Some thermoplastic adhesive materials will also penetrate into both the absorbent particulate polymer material 66 and 74 and the substrates 64 and 72, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 14 is dry. The thermoplastic adhesive material 68 and 76 may also be referred to as a hot melt adhesive.

Without wishing to be bound by theory, it has been found that those thermoplastic adhesive materials which are most useful for immobilizing the absorbent particulate polymer material 66 and 74 combine good cohesion and good adhesion behavior. Good adhesion may promote good contact between the thermoplastic adhesive material 68 and 76 and the absorbent particulate polymer material 66 and 74 and the substrates 64 and 72. Good cohesion reduces the likelihood that the adhesive breaks, in particular in response to external forces, and namely in response to strain. When the absorbent core 14 absorbs liquid, the absorbent particulate polymer material 66 and 74 swells and subjects the thermoplastic adhesive material 68 and 76 to external forces. In certain embodiments, the thermoplastic adhesive material 68 and 76 may allow for such swelling, without breaking and without imparting too many compressive forces, which would restrain the absorbent particulate polymer material 66 and 74 from swelling.

In accordance with certain embodiments, the thermoplastic adhesive material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or −6° C.>Tg<16° C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic adhesive material 68 and 76 is present in the form of fibers. In some embodiments, the fibers will have an average thickness of about 1 to about 50 micrometers or about 1 to about 35 micrometers and an average length of about 5 mm to about 50 mm or about 5 mm to about 30 mm. To improve the adhesion of the thermoplastic adhesive material 68 and 76 to the substrates 64 and 72 or to any other layer, in particular any other non-woven layer, such layers may be pre-treated with an auxiliary adhesive.

In certain embodiments, the thermoplastic adhesive material 68 and 76 will meet at least one, or several, or all of the following parameters:

An exemplary thermoplastic adhesive material 68 and 76 may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more then 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

Figure 9:
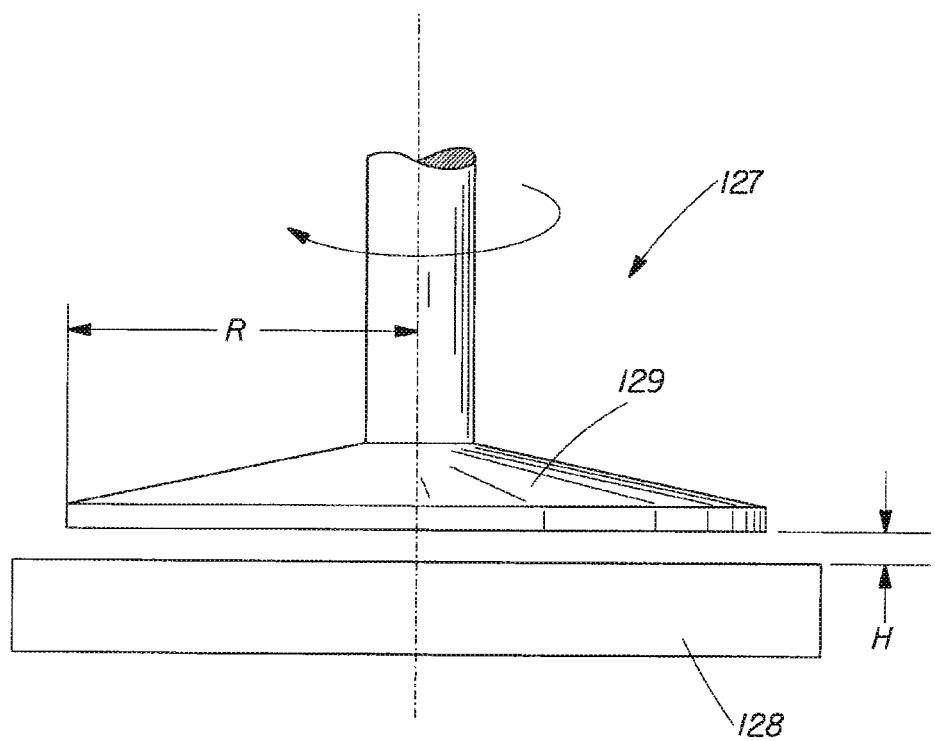
FIG. 9 is a schematic representation of a rheometer.

G' is measured using a rheometer as schematically shown in FIG. 9 for the purpose of general illustration only. The rheometer 127 is capable of applying a shear stress to the adhesive and measuring the resulting strain (shear deformation) response at constant temperature. The adhesive is placed between a Peltier-element acting as lower, fixed plate 128 and an upper plate 129 with a radius R of e.g., 10 mm, which is connected to the drive shaft of a motor to generate the shear stress. The gap between both plates has a height H of e.g., 1500 micron. The Peltier-element enables temperature control of the material (+0.5° C.). The strain rate and frequency should be chosen such that all measurements are made in the linear viscoelastic region.

The absorbent core 14 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72. The auxiliary glue may also aid in immobilizing the absorbent particulate polymer material 66 and 74 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary glue may be applied to the substrates 64 and 72 by any suitable means, but according to certain embodiments, may be applied in about 0.5 to about 1 mm wide slots spaced about 0.5 to about 2 mm apart.

The cover layer 70 shown in FIG. 4 may comprise the same material as the substrates 64 and 72, or may comprise a different material. In certain embodiments, suitable materials for the cover layer 70 are the non-woven materials, typically the materials described above as useful for the substrates 64 and 72.

Figure 10:
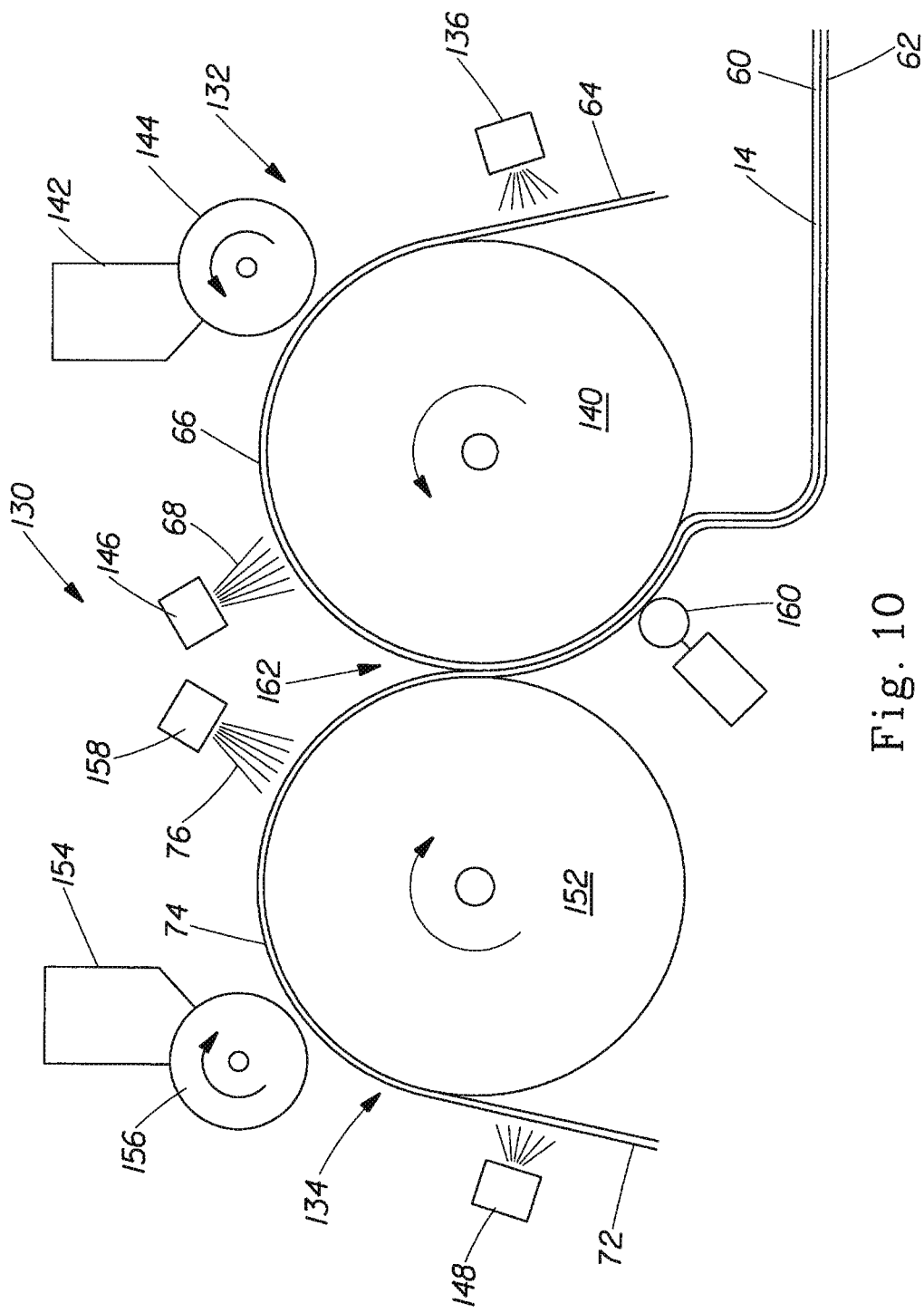
FIG. 10 is a schematic illustration of a process for making an absorbent core in accordance with an embodiment of this invention.

A printing system 130 for making an absorbent core 14 in accordance with an embodiment of this invention is illustrated in FIG. 10 and may generally comprise a first printing unit 132 for forming the first absorbent layer 60 of the absorbent core 14 and a second printing unit 134 for forming the second absorbent layer 62 of the absorbent core 14.

The first printing unit 132 may comprise a first auxiliary adhesive applicator 136 for applying an auxiliary adhesive to the substrate 64, which may be a nonwoven web, a first rotatable support roll 140 for receiving the substrate 64, a hopper 142 for holding absorbent particulate polymer material 66, a printing roll 144 for transferring the absorbent particulate polymer material 66 to the substrate 64, and a thermoplastic adhesive material applicator 146 for applying the thermoplastic adhesive material 68 to the substrate 64 and the absorbent particulate polymer 66 material thereon.

The second printing unit 134 may comprise a second auxiliary adhesive applicator 148 for applying an auxiliary adhesive to the second substrate 72, a second rotatable support roll 152 for receiving the second substrate 72, a second hopper 154 for holding the absorbent particulate polymer material 74, a second printing roll 156 for transferring the absorbent particulate polymer material 74 from the hopper 154 to the second substrate 72, and a second thermoplastic adhesive material applicator 158 for applying the thermoplastic adhesive material 76 to the second substrate 72 and the absorbent particulate polymer material 74 thereon.

The printing system 130 also includes a guide roller 160 for guiding the formed absorbent core from a nip 162 between the first and second rotatable support rolls 140 and 152.

The first and second auxiliary applicators 136 and 148 and the first and second thermoplastic adhesive material applicators 146 and 158 may be a nozzle system which can provide a relatively thin but wide curtain of thermoplastic adhesive material.

Figure 11:
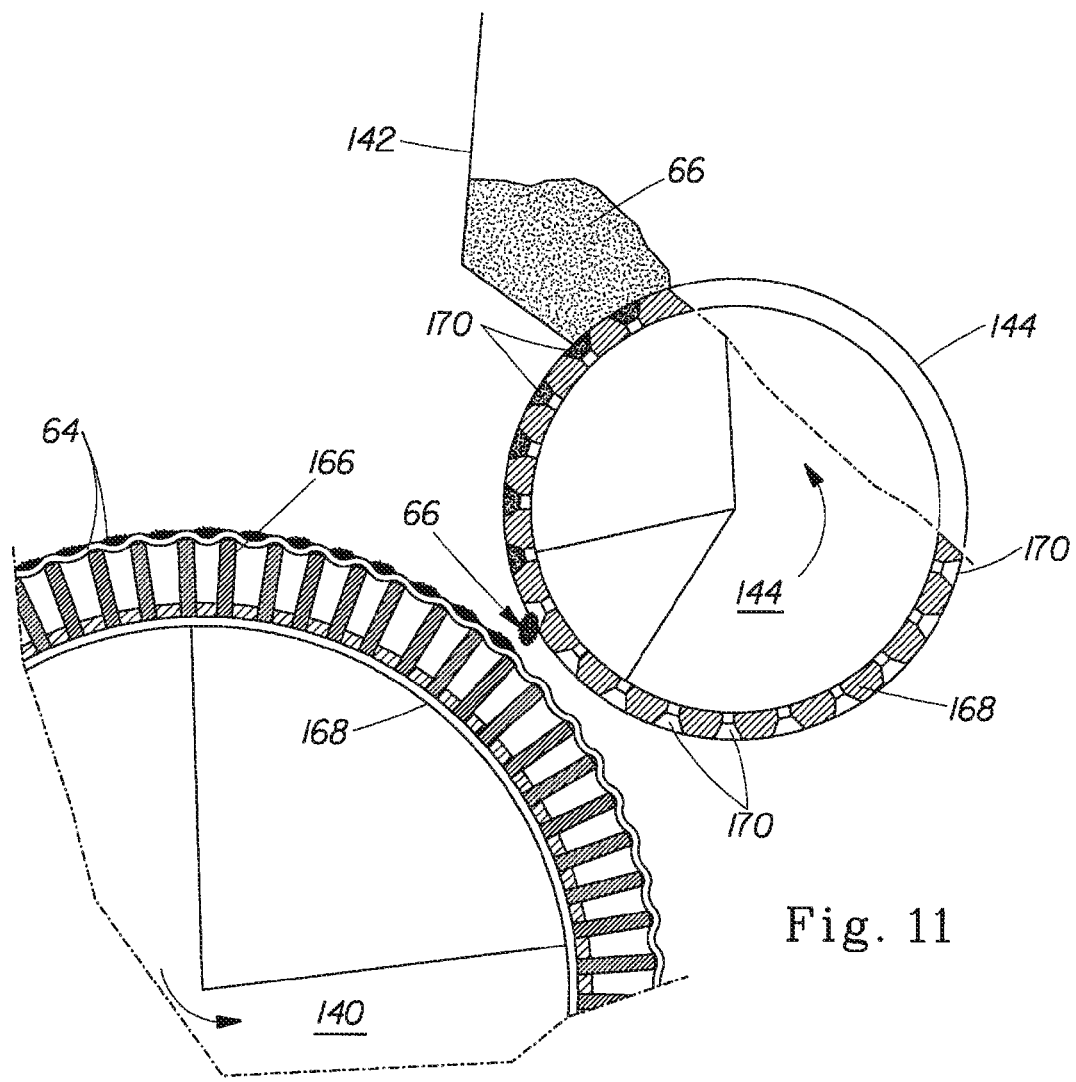
FIG. 11 is a partial sectional view of an apparatus for making an absorbent core in accordance with an embodiment of this invention.
Figure 14:
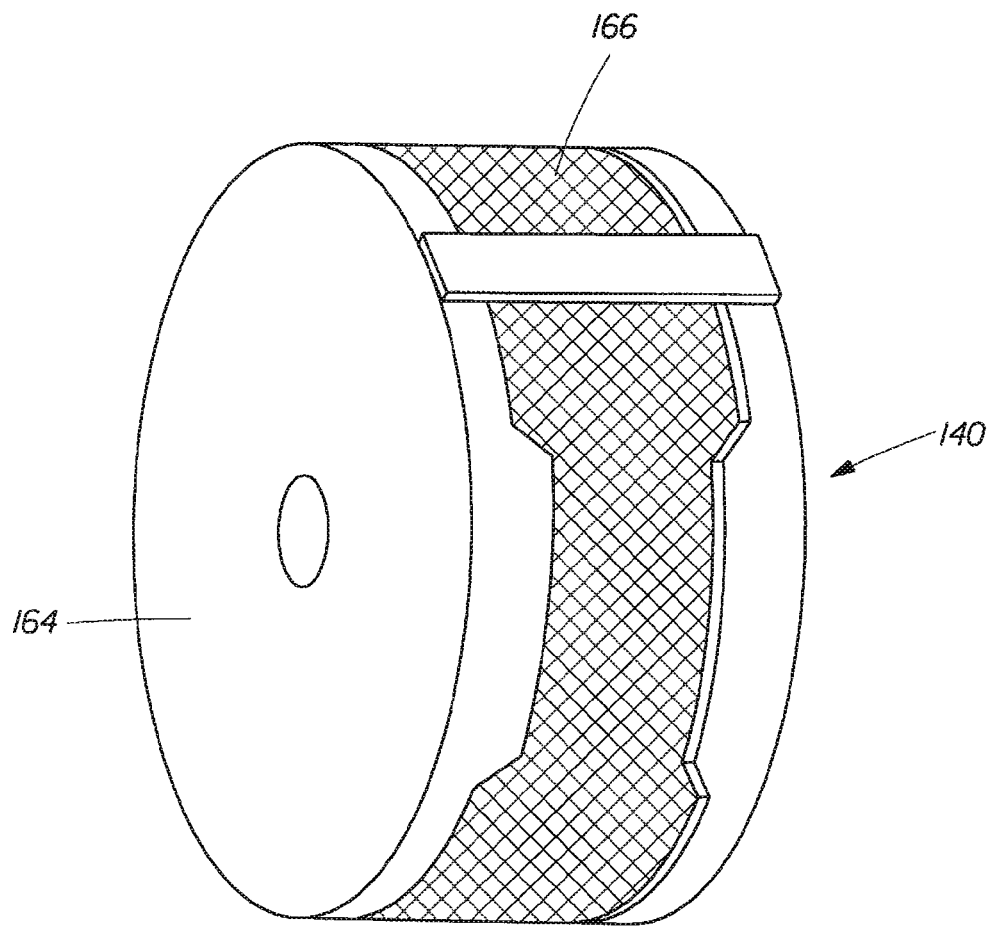
FIG. 14 is a perspective view of the supporting roll illustrated in FIG. 12.

Turning to FIG. 11, portions of the first hopper 142, first support roll 140, and first printing roll 144 are illustrated. As also shown in FIG. 14, the first rotatable support roll 140, which has the same structure as the second rotatable support roll 152, comprises a rotatable drum 164 and a peripheral vented support grid 166 for receiving the first substrate 64.

Figure 12:
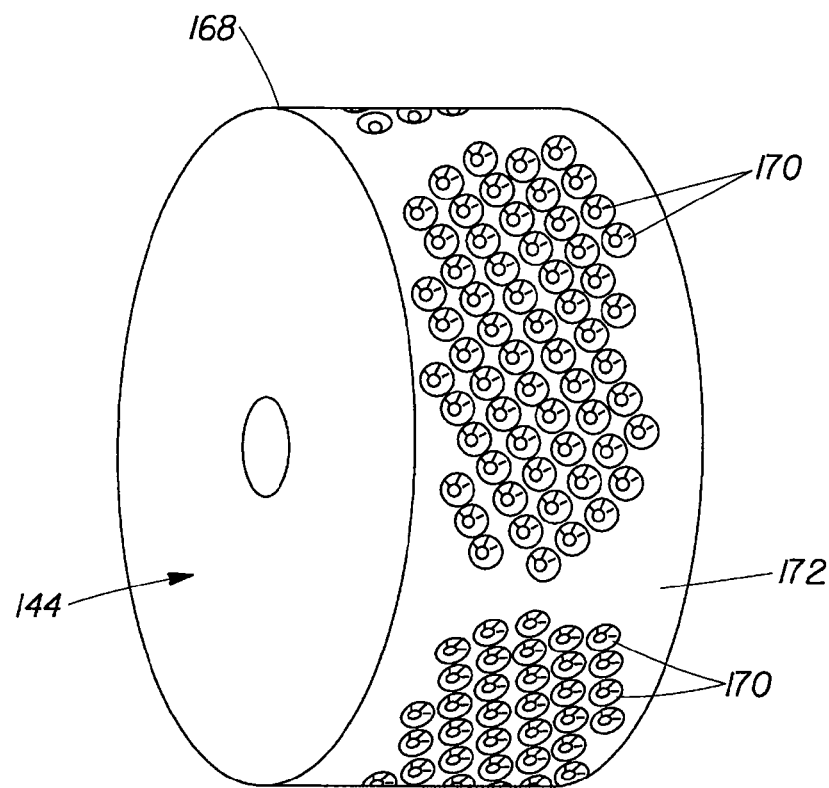
FIG. 12 is a perspective view of the printing roll illustrated in FIG. 11.
Figure 13:
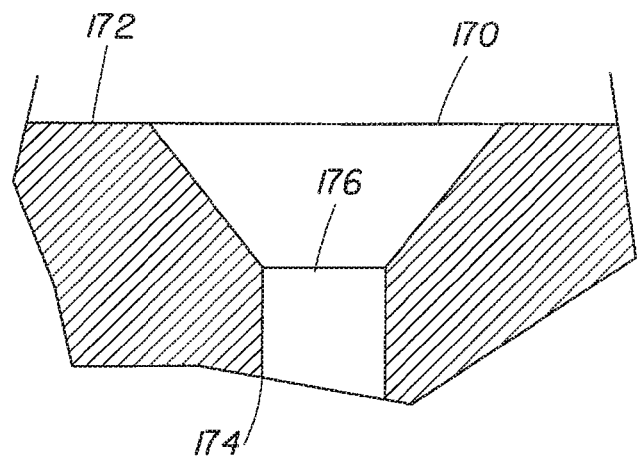
FIG. 13 is a partial sectional view of the printing roll illustrated in FIG. 12 showing an absorbent particulate polymer material reservoir.

As also illustrated in FIG. 12, the first printing roll 144, which has the same structure as the second printing roll 156, comprises a rotatable drum 168 and a plurality of absorbent particulate polymer material reservoirs 170 in a peripheral surface 172 of the drum 168. The reservoirs 170 best illustrated in FIG. 13, may have a variety of shapes, including cylindrical, conical, or any other shape. The reservoirs 170 may lead to an air passage 174 in the drum 168 and comprise a vented cover 176 for holding adhesive particulate polymer material 66 in the reservoir and preventing the adhesive particulate polymer material 66 from falling or being pulled into the air passage 174.

Figure 5:
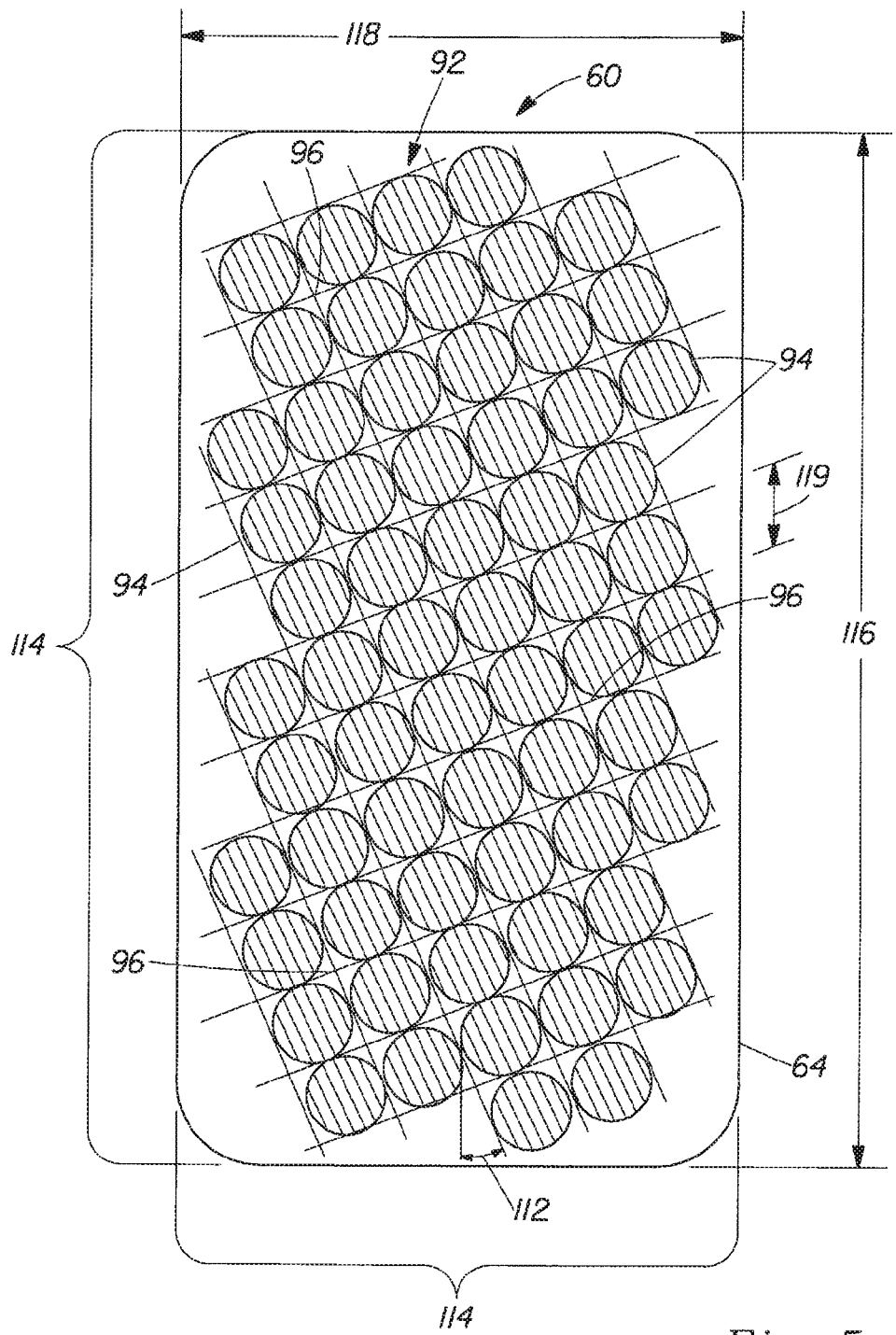
FIG. 5 is a plan view of the absorbent core layer illustrated in FIG. 3.
Figure 6:
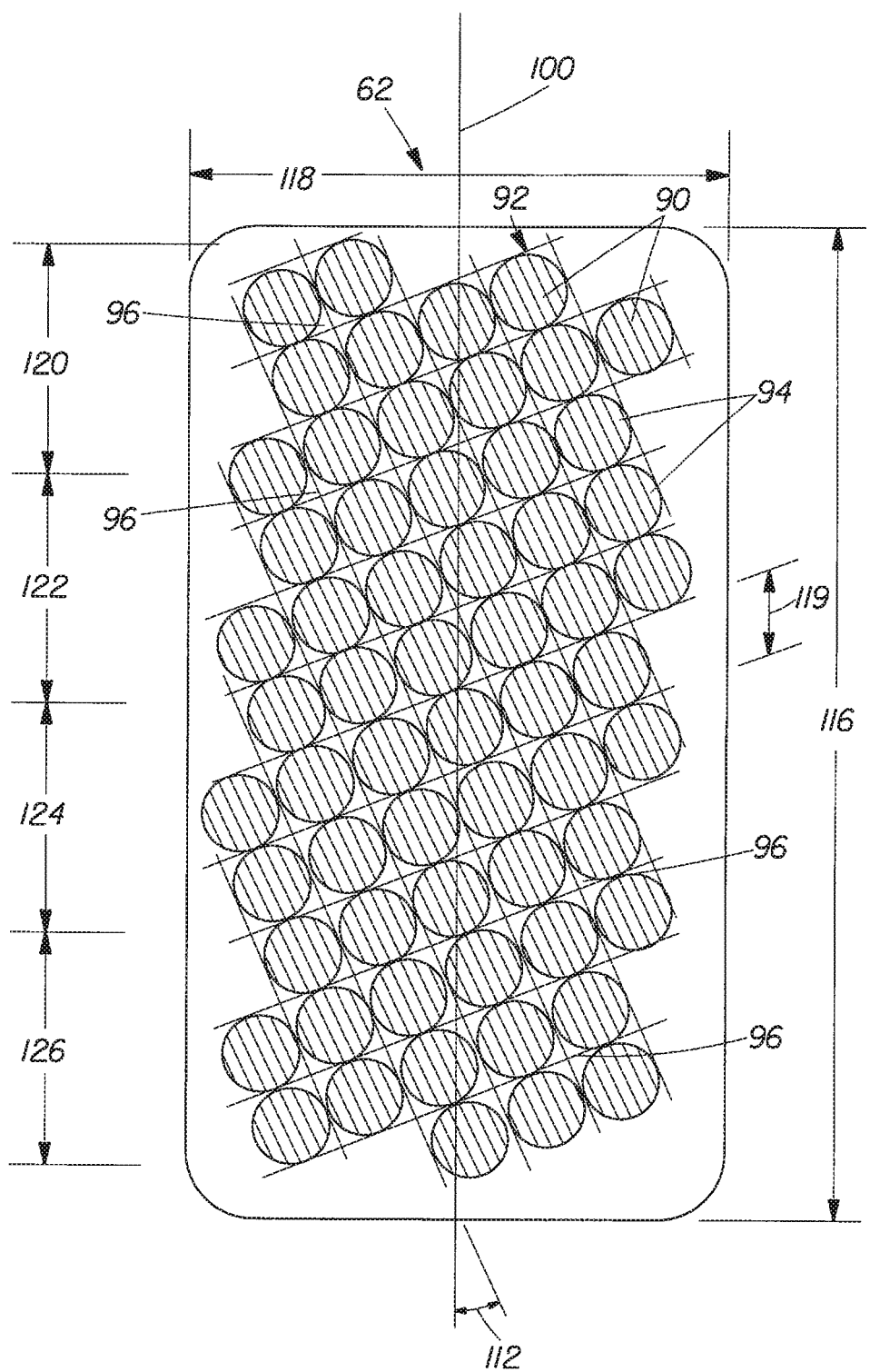
FIG. 6 is a plan view of a second absorbent core layer in accordance with an embodiment of this invention.

In operation, the printing system 130 receives the first and second substrate 64 and 72 into the first and second printing units 132 and 134, respectively, the first substrate 64 is drawn by the rotating first support roll 140 past the first auxiliary adhesive applicator 136 which applies the first auxiliary adhesive to the first substrate 64 in a pattern such as described hereinabove. A vacuum (not shown) within the first support roll 140 draws the first substrate 64 against the vertical support grid 166 and holds the first substrate 64 against the first support roll 140. This presents an uneven surface on the first substrate 64. Due to gravity, or by using the vacuum means, the substrate 64 will follow the contours of the uneven surface and thereby the substrate 64 will assume a mountain and valley shape. The absorbent particulate polymer material 66 may accumulate in the valleys presented by the substrate 64. The first support roll 140 then carries the first substrate 64 past the rotating first printing roll 144 which transfers the absorbent particulate polymer material 66 from the first hopper 142 to the first substrate 64 in the grid pattern 92 which is best illustrated in FIGS. 5 and 6. A vacuum (not shown) in the first printing roll 144 may hold the absorbent particulate polymer material 66 in the reservoirs 170 until time to deliver the absorbent particulate polymer material 66 to the first substrate 64. The vacuum may then be released or air flow through the air passages 174 may be reversed to eject the absorbent particulate polymer material 66 from the reservoirs and onto the first substrate 64. The absorbent particulate polymer material 66 may accumulate in the valleys presented by the substrate 64. The support roll 140 then carries the printed first substrate 64 past the thermoplastic adhesive material applicator 136 which applies the thermoplastic adhesive material 68 to cover the absorbent particulate polymer material 66 on the first substrate 64.

Hence, the uneven surface of the vented support grid 166 of the support rolls 140 and 152 determines the distribution of absorbent particulate polymeric material 66 and 74 throughout the absorbent core 14 and likewise determines the pattern of junction areas 96.

Meanwhile, the second rotatable support roll draws the second substrate 72 past the second auxiliary adhesive applicator 148 which applies an auxiliary adhesive to the second substrate 72 in a pattern such as is described hereinabove. The second rotatable support roll 152 then carries the second substrate 72 past the second printing roll 156 which transfers the absorbent particulate polymer material 74 from the second hopper 154 to the second substrate 72 and deposits the absorbent particulate polymer material 74 in the grid pattern 92 on the second substrate 72 in the same manner as described with regard to the first printing unit 132 above. The second thermoplastic adhesive material applicator 158 then applies the thermoplastic adhesive material 76 to cover the absorbent particulate polymer material 74 on the second substrate 72. The printed first and second substrates 64 and 72 then pass through the nip 162 between the first and second support rolls 140 and 152 for compressing the first absorbent layer 60 and second absorbent layer 62 together to form the absorbent core 14.

In an optional further process step a cover layer 70 may be placed upon the substrates 64 and 72, the absorbent particulate polymer material 66 and 74, and the thermoplastic adhesive material 68 and 76. In another embodiment, the cover layer 70 and the respective substrate 64 and 72 may be provided from a unitary sheet of material. The placing of the cover layer 70 onto the respective substrate 64 and 72 may then involve the folding of the unitary piece of material.

Absorbent articles such as the diapers 10 made in accordance with embodiments of this invention may be folded and packaged for distribution and sale. Absorbent articles are typically bi-folded. After folding, the folded absorbent articles may be stacked to form a stack comprising a plurality of absorbent articles. The stack may then be compressed and encased in a packaging material such as a bag, a pouch, a box, or the like.

Figure 15A:
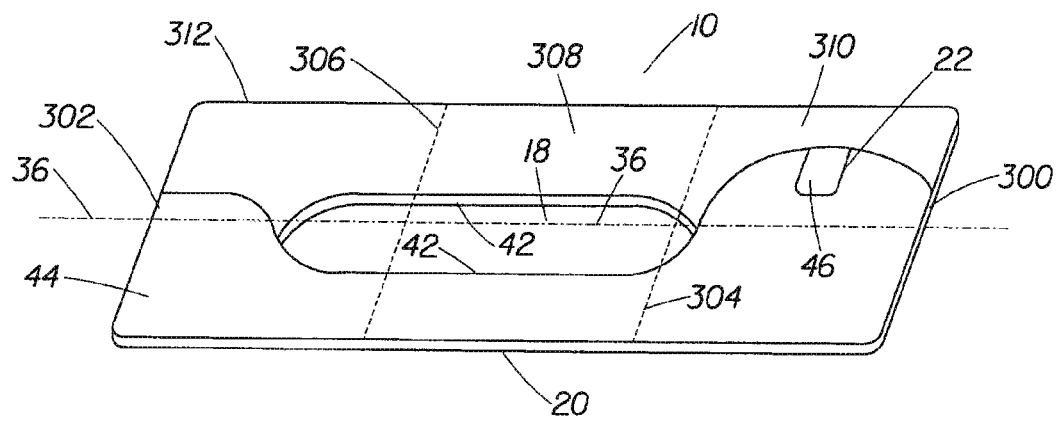
Figure 15B:
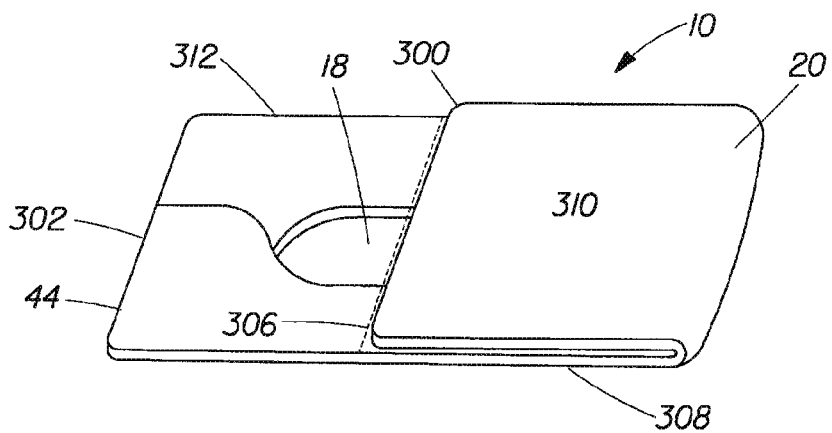
Figure 15C:
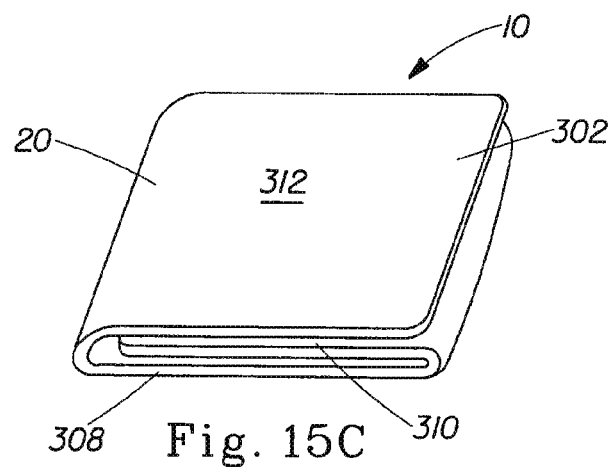
FIG. 15C is a perspective view of the diaper illustrated in FIG. 1 with sides and both ends folded in to form a tri-fold diaper.

In accordance with an embodiment of this invention as illustrated in FIGS. 15A-15C, the diaper 10 may be tri-folded to reduce the height of the folded diaper 10. Tri-folded diapers create opportunities for efficient and convenient packaging, transportation, storage, and display.

Turning to FIG. 15A, the diaper 10 is shown laid out flat and extends from a first end 300 to a second end 302 with the longitudinal axis 36 of the diaper extending from the first end 300 to the second end 302, the topsheet 18 facing upwardly, and the longitudinal edges 42 folded inwardly over the topsheet 18. To form a tri-fold configuration, the diaper 10 may be folded substantially perpendicularly to the longitudinal axis 36 of the diaper 10 along a first fold line 304 and a second fold line 306 spaced from the first fold line 304 so as to form a central section 308 extending from the first fold line 304 to the second fold line 306, a first end section 310 extending from the first fold line 304 to the first end 300 of the diaper 10, and a second end section 312 extending from the second fold line 306 to the second end 302 of the diaper so that the first section 310, central section 308, and the second section 312 are superposed to one another as illustrated in progression in FIGS. 15B and 15C.

To tri-fold the diaper 18, the first end 300 of the diaper 10 may be folded along the first fold line 304 so that the first section 310 of the diaper overlays the central section 308 and is substantially coextensive with the central section 308. This is best illustrated in FIG. 15B. Next, as illustrated in FIG. 15C, the second end section 312 of the diaper 10 is folded along the second fold line 306 so that the second end section 312 overlays the first section 310 of the diaper 10 and is substantially coextensive with both the first section 310 and the central section 308.

Optionally, of course, the second end 312 may be folded over the central section 308 first, followed by folding the first section 310 over the second section 312 or the first section 310 of the diaper 10 may be folded over one side of the central section 308 and the second section 312 of the diaper 10 may be folded in an opposite direction over the other side of the central section 308.

Figure 16:
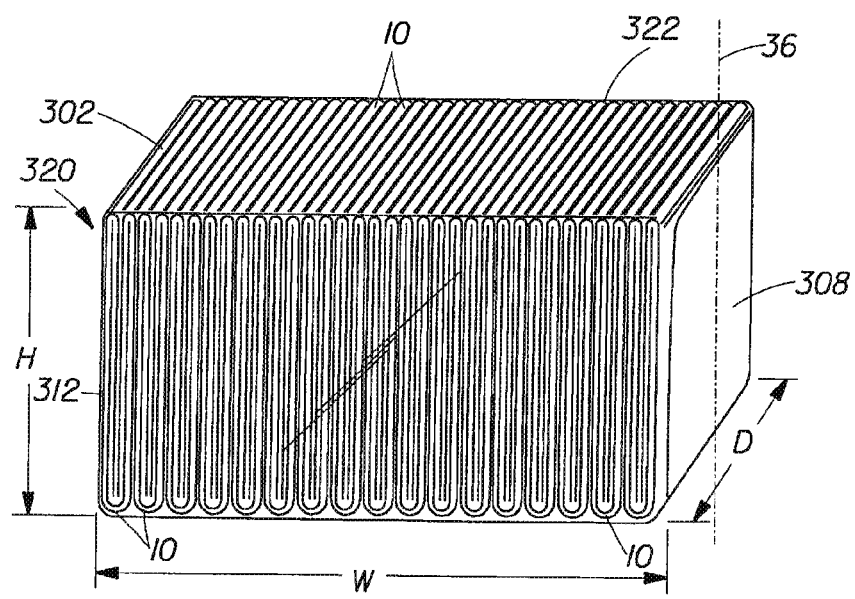
FIG. 16 is a perspective view of a diaper package in accordance with an embodiment of this invention.

After tri-folding, the tri-folded diapers 10 may be stacked to form a stack comprising a plurality of the diapers 10 such that the diapers are in a substantially superposed stacked configuration. This stack of tri-folded diapers 10 may then be compressed in a manner well known to those skilled in the art and packaged to form a diaper package 320 as illustrated in FIG. 16. The diapers 10 may be packaged in a packaging material 322 such as a flexible bag or pouch or a box or the like. The diaper package 320 illustrated in FIG. 16 has a width W, a height H extending perpendicularly to the width W, and a depth D extending substantially perpendicularly to both width W and the height H. The height H of the diaper package 320 is substantially parallel to the longitudinal axis 36 of the diapers 10.

The diaper package 320 may form part of an array 324 of diaper packages arranged in accordance with diaper size. Diapers are typically sized according to the size of the wearer and the size of the wearer is typically gauged in weight of the wearer. Table 1 below, for example, illustrates a typical schedule of diaper sizes ranging from a size N for a wearer up to 10 pounds to a size 7 for a wearer weighing 41 or more pounds.

TABLE 1

| Size Indicator | Weight Range Indicator |
| --- | --- |
| N | Up to 10 lbs (up to 4.5 kg) |
| 1 | 8-14 lbs (4-6 kg) |
| 2 | 12-18 lbs (5-8 kg) |
| 3 | 16-28 lbs (7-13 kg) |
| 4 | 22-37 lbs (10-17 kg) |
| 5 | 27+ lbs (12+ kg) |
| 6 | 35+ lbs (16+ kg) |
| 7 | 41+ lbs (19+ kg) |

Figure 17:
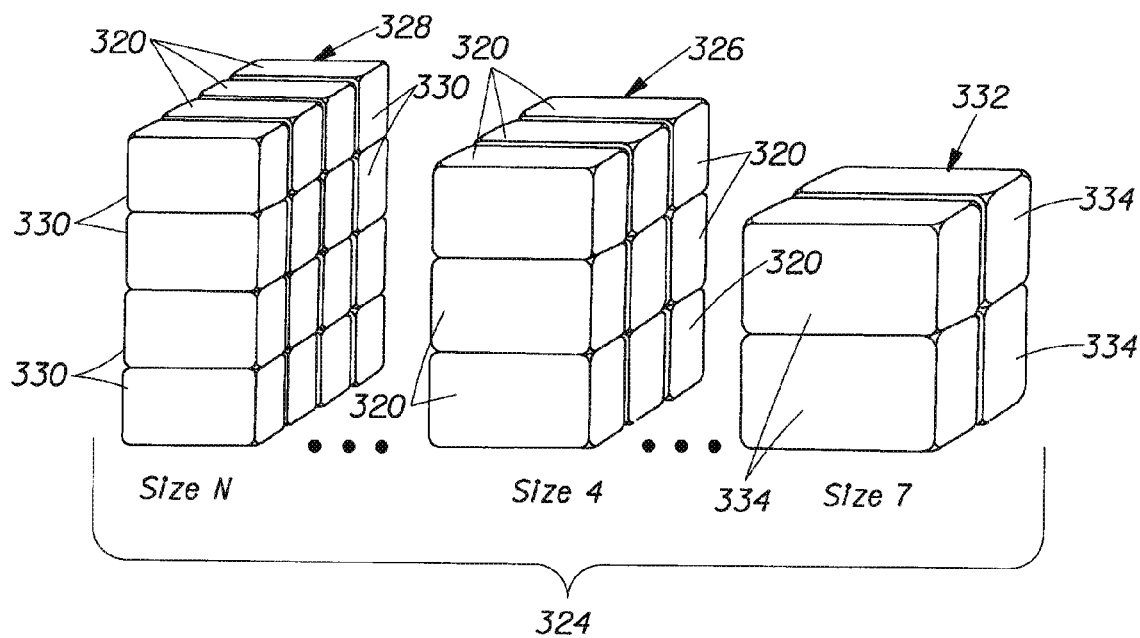
FIG. 17 is a partial perspective view of an array of diaper packages in accordance with an embodiment of this invention.

The array 24 illustrated in FIG. 17 shows how diaper packages may be arranged according to size. In the array 324 illustrated in FIG. 17, the diaper package 320 may comprise a stack of size 4 diaper packages 326. The array 324 may extend from a stack 328 of size N diaper packages 330 to a stack 332 of size 7 diaper packages 334. The reduced height H of the diapers 10 from tri-folding the diapers 10, as opposed to bi-folding, may create opportunities for different arrangements of diaper packages within the array 324 which may allow for efficient and convenient transportation, storage, and/or display of the diaper packages.

The diapers 10 in the diaper package 320 may occupy a volume in the package that is relatively small due to the substantially cellulose free absorbent core 14 in the diaper 10. For example, in a size 4, under base compression of 2500 to 5000 N, the diapers 10 may occupy a volume in the diaper package 320 of less than about 200 cc per diaper 10, less than about 190 cc per diaper 10, less than about 180 cc per diaper 10, or less than about 175 cc per diaper 10. Further, in a size 4, under high compression of 6000 to 10000 N, the diapers 10 may occupy a volume in the diaper package 320 of less than about 180 cc per diaper 10, less than about 160 cc per diaper 10, less than about 150 cc per diaper 10, or less than about 140 cc per diaper 10. For different size diapers, the volume occupied by the diapers when packaged would be different than the volume occupied by the size 4 diaper. Smaller size diapers would occupy a smaller volume and larger size diapers would occupy a larger volume, but due to the thinness imparted by the substantially cellulose free pre-absorbent cores 14 in the diapers 10, the volume occupied by such diapers 10 in packaging is relatively small and, in combination with tri-folding, creates opportunities for efficient and convenient packaging, transportation, storage, and display the diapers 10.

Table 2 below contains physical measurements of a packaged stack of bi-folded conventional diapers made with an absorbent core which is not substantially cellulose free (Comp 1) and packaged stacks of tri-folded diapers having a substantially cellulose free absorbent core in accordance with embodiments of this invention (Examples 1 and 2). The physical measurements were made with the Universal Diaper Packaging Tester described herein below. Example 1 is a 30 count stack of tri-folded diapers comprising a substantially cellulose free absorbent core and was subjected to a base compression of 2500 to 5000 N and Example 2 is a 36 count stack of tri-folded diapers comprising a substantially cellulose free absorbent core and was subjected to a high compression of 6000 to 10000 N. As can be seen from data in Table 2, the bag heights of Examples 1 and 2 made in accordance with embodiments of this invention are substantially less than the bag height of the diaper stack in Comparative Example 1 and, accordingly, the volume in the packages occupied by the diapers in Examples 1 and 2 is much less than the volume occupied by the diapers in the stack of Comparative Example 1.

Note that the compression of a stack of diapers in a package can be defined by In-Process-Stack-Height (IPSH). IPSH is the lowest caliper of a stack of 10 pads during main compression of the packaging process or by compression force (N) measured during main compression. The IPSH of Example 1 was 56 mm and the IPSH of Example 2 was 50. Further, diaper stack height may be measured by In-Bag-Stack-Height (IBSH). The IBSH is the caliper of 10 pads within the packed bag, calculated by dividing the filled bag width by the numbers of pads per packed stack times 10. The lower the IBSH, the thinner and more compressed is the stacked product.

TABLE 2

| | Comp. 1<br>Size 4<br>30 count, 1-Stack<br>Not CF[1]<br>Base Compression | Example 1<br>Size 4<br>30 count, 1-Stack<br>CF & TF[2]<br>Base Compression | Example 2<br>Size 4<br>36 count, 1-Stack<br>CF & TF<br>High Compression |
| --- | --- | --- | --- |
| Bag width (linear shelf direction) (mm) | 265 | 273.7 | 279.6 |
| Bag Depth (Front to Back) mm | 118 | 113.3 | 112.3 |

TABLE 2-continued

| | Comp. 1<br>Size 4<br>30 count, 1-Stack<br>Not CF[1]<br>Base Compression | Example 1<br>Size 4<br>30 count, 1-Stack<br>CF & TF[2]<br>Base Compression | Example 2<br>Size 4<br>36 count, 1-Stack<br>CF & TF<br>High Compression |
|---|---|---|---|
| Bag Height mm | 233 | 170.8 | 172.1 |
| Volume (cc) | 7285.91 | 5294.8 | 5402.10 |
| cc/diaper | 242.9 | 176.5 | 150.1 |

[1]CF means cellulose free.
[2]TF means tri-folded.

Table 3 below contains physical measurements of packaged stacks of commercially available bi-folded conventional diapers made with an absorbent core which is not substantially cellulose free and a packaged stack of tri-folded diapers having a substantially cellulose free absorbent core in accordance with an embodiment of this invention (Example 3 below). The physical measurements were made with the Universal Diaper Packaging Tester described herein below. Example 3 is a 30 count stack of tri-folded diapers comprising a substantially cellulose free absorbent core and was subjected to a base compression of 2500-5000 N. As can be seen from data in Table 3, the bag height of Example 3 made in accordance with an embodiment of this invention is substantially less than the bag heights of the commercially available diaper stacks. Accordingly, the volume in the packages occupied by the diapers in Example 3 is much less than the volume occupied by the diapers in the commercially available diaper packages.

TABLE 3

| Product | Size | Pkg Count | Height | Width | Depth | Volume | Vol(cc)/Diaper |
|---|---|---|---|---|---|---|---|
| Huggies Snug & Dry | 4 | 34 | 22.8 | 29.6 | 11.8 | 7963.6 | 234.2 |
| Huggies Natural Fit | 4 | 30 | 21.5 | 33.6 | 10.6 | 7657.4 | 255.2 |
| Parent's Choice (Arquest) | 4 | 34 | 22.7 | 30.9 | 11.8 | 8276.9 | 243.4 |
| White Cloud (Tyco Healthcare) | 4 | 34 | 23.5 | 32.2 | 10.8 | 8172.4 | 240.4 |
| Little Ones (Tyco Healthcare) | 4 | 34 | 22.5 | 30.9 | 11.6 | 8064.9 | 237.2 |
| Cruisers Plus | 4 | 30 | 23.3 | 26.5 | 11.8 | 7285.9 | 242.9 |
| Example 3 | 4 | 30 | 17.8 | 25.6 | 10.9 | 4966.9 | 165.6 |

Figure 18:
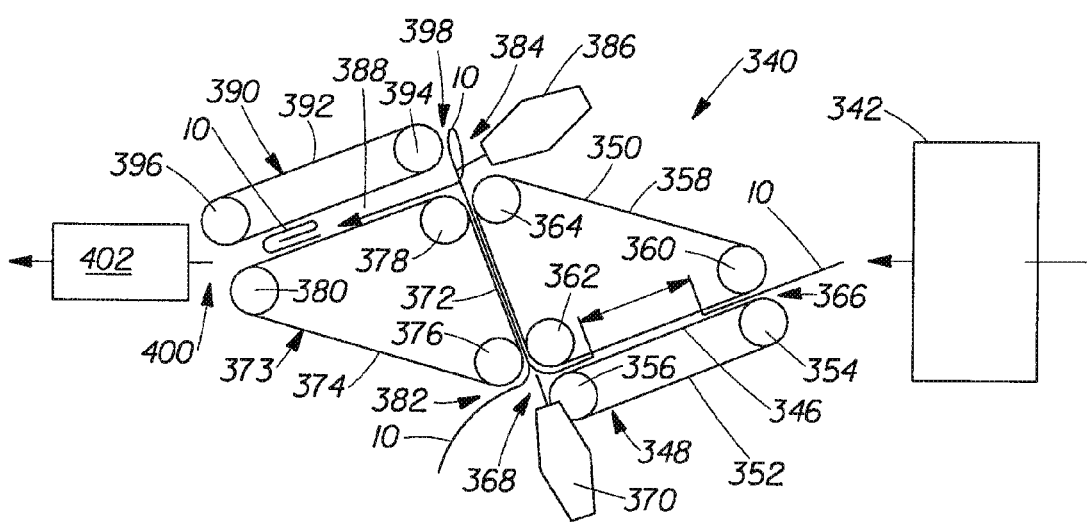
FIG. 18 is a schematic illustration of a diaper tri-folding system.

A diaper tri-folding system 340 for tri-folding the diapers 10 in accordance with an embodiment of this invention is illustrated. As will be appreciated by those skilled in the art, there are many possible configurations of diaper tri-folding systems other than that illustrated in FIG. 18. The diaper tri-folding system 340 is one possible embodiment.

The diaper tri-folding system 340 receives the diapers 10 in series from a diaper assembly system 342 into a first conveyor path 346. The first conveyor path 346 extends between a first conveyor 348 and a second conveyor 350 juxtaposed to the first conveyor 348. The first conveyor 348 comprises a conveyor belt 352 traveling about a first wheel 354 and a second wheel 356 spaced from the first wheel 354. The second conveyor 350 is disposed above the first conveyor 348 and comprises a conveyor belt 350 traveling around a triangular arrangement of a first wheel 360, a second wheel 362, and a third wheel 364. The first conveyor path 346 extends between the first conveyor 348 and a second conveyor 350 from an inlet 366 proximate the first wheel 354 of the first conveyor 348 and the first wheel 360 of the second conveyor 350 to an outlet 368 proximate the second wheel 356 of the first conveyor 348 and the second wheel 362 of the second conveyor 350.

A first fold tucker blade 370 is positioned proximate the outlet 368 of the first conveyor path and substantially perpendicularly to the first conveyor path 346. The first fold tucker blade 370 is disposed for reciprocating operation to fold the diaper 10 along the first fold line 304.

The tri-folding system also includes a second conveyor path 372 positioned substantially perpendicularly to the first conveyor path 346 and extending from proximate the outlet 368 of the first conveyor path 346 between the second conveyor 350 and a third conveyor 373. The third conveyor 373 comprises a conveyor belt 374 driven around a triangular configuration of a first wheel 376, a second wheel 378, and a third wheel 380. The third conveyor 373 is juxtaposed to the second conveyor 350 and the second conveyor path 372 extends from an inlet 382 proximate the second wheel 362 of the second conveyor 360 and the first wheel 376 of the third conveyor 373 to an outlet 384 proximate the third wheel 364 of the second conveyor 350 and the second wheel 378 of the third conveyor 373.

A second fold tucker blade 386 is positioned substantially perpendicularly to the second conveyor path 372 proximate the outlet 384 of the second conveyor path 372. The second fold tucker blade 386 is positioned for reciprocating operation to fold the diapers 10 along the second fold line 306 to complete the tri-folding of the diapers 10.

The tri-folding system 340 also comprises a third conveyor path 388 extending substantially perpendicularly from the second conveyor path 372 from proximate the outlet 384 of the second conveyor path 372. The third conveyor path 388 extends between the third conveyor 373 and a fourth conveyor 390 juxtaposed to the third conveyor 373. The fourth conveyor 390 comprises a conveyor belt 392 driven around a first wheel 394 and a second wheel 396 spaced from the first wheel 394. The third conveyor path 388 extends from an inlet 398 proximate the second wheel 378 of the third conveyor 373 and the first wheel 394 of the fourth conveyor 390 to an outlet 400 proximate the third wheel 380 of the third conveyor 373 and the second wheel 396 of the fourth conveyor 390.

The tri-folding system 340 leads to a diaper packaging system 402, which is not illustrated herein in detail as such systems are well known.

The tri-folding 340 tri-folds diapers 10 received from the diaper assembly system 342 by first receiving the diapers 10 in a substantially flat configuration with the longitudinal edges 342 folded inwardly over the topsheet 18. The diapers 10 are received between the first and second conveyors 348 and 350 through the inlet 356 of the first conveyor path and are transported along the first conveyor path 346 through the outlet 368 of the first conveyor path 346 so that the second end 302 of the diaper 10 extends outwardly beyond the outlet 368 of the first conveyor path 346. When the diaper 10 extends far enough through the outlet 368 of the first conveyor path 346 for the first fold tucker blade 370 to be aligned with the first fold line 304 of the diaper 10, the first fold tucker blade 370 reciprocates forward, folds the diaper 10 along the first fold line 304 such that the first section 310 of the diaper 10 overlays the central section 308 of the diaper 10, and thrusts the diaper 10 through the inlet 382 of the second conveyor path 372. The second and third conveyors 350 and 373 carry the diaper 10 along the second conveyor path 372 and through the outlet 384 of the second conveyor path 372 such that the second fold tucker blade 386 is aligned with the second oldline 306 of the diaper 10. The second fold tucker blade 386 then reciprocates forward and folds the diaper 10 along the second fold line 306 so that the second section 312 of the diaper 10 overlays the first section 310 of the diaper 10 and thrusts the tri-folded diaper 10 through the inlet 398 of the third conveyor path 388. The third and fourth conveyors 373 and 390 then carry the tri-folded diaper 10 along the third conveyor path 388 until the tri-folded diaper is ejected through the outlet 400 of the third conveyor path 388 and the diaper is a received by the packaging system 402.

Figure 19:
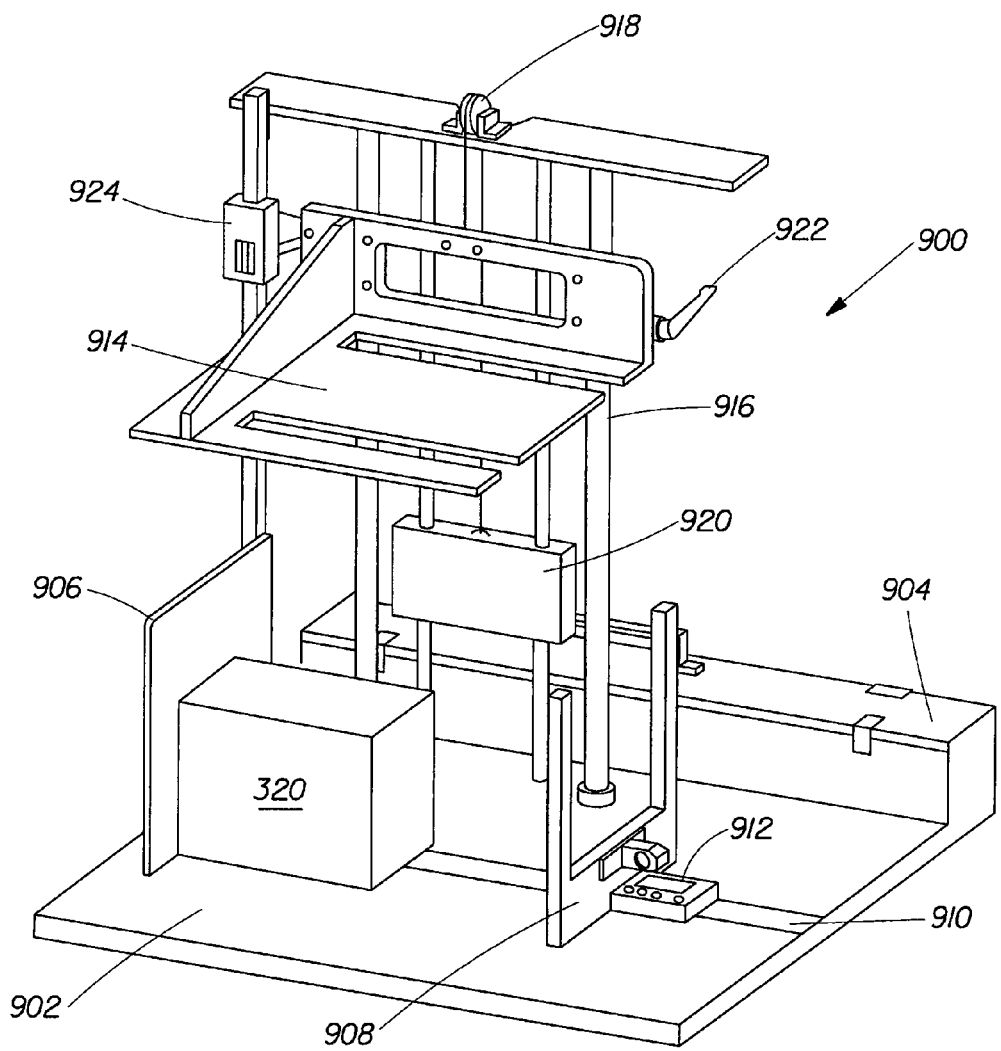
FIG. 19 is a perspective view of a universal diaper packaging tester.

The diaper package 320 dimensions (Length/Width/Depth (aka Front-to-Back)) were measured using a "Universal Diaper Packaging Tester" (UDPT) 900 which is illustrated in FIG. 19. The UDPT 900 comprises a base 902 with a storage box 904 on the back of the base 902. A vertical anchored plate 906 is mounted to the base 902 proximate one end of the base 902 and a horizontal sliding plate 908 is mounted to the base 902 in a horizontal track 910. A first digital meter 912 is disposed along the horizontal track 910 adjacent the horizontal sliding plate 908. A vertical sliding plate 914 is slidably mounted above the base 902 and over the horizontal track 910 to a vertical track 916 which is mounted to the base 902 between the horizontal track 910 and the storage box 904. A pulley 918 mounted to the vertical track 916 connects the vertical sliding plate 914 to a suspended weight 920 which counter-balances the weight of the vertical sliding plate 914 to assure that no downward force is added from the vertical sliding plate 914 assembly to the diaper package 320 at all times. A stopper 922 is mounted to the vertical sliding plate 914 for locking the vertical sliding plate 914 to the vertical track 916. A second digital meter 924 is mounted to the vertical track 916 proximate the vertical sliding plate 914.

A UDPT is Available from Matsushita Industry Co. LTD, 7-21-101, Midorigaoka-cho, Ashiya-city, Hyogo Japan 659-0014; Tel. (81) 797 34 3367; Drawing: M-ROEL-01000-B; Region-ID: UDPT-EU-1/UDPT-NA-1/UDPT-LA-1.

The UDPT test procedure is as follows:
The UDPT 900 is calibrated by (1) pulling down the vertical sliding plate 914 until its bottom touches the base 902, setting the second digital meter 924 of the vertical sliding plate 914 to zero mark, and raising the vertical sliding plate 914 away from the base 902.

The diaper package 320 width W (see FIG. 16) is the maximum distance between the two highest bulging points along the same compression stack axis of the diaper package 320. The package height H is the maximum distance between the bottom panel and the highest point of the top panel of the diaper package. The package depth (aka front-to-back) is the maximum distance between the front and back panels of a diaper package 320.

To measure the diaper package 320 dimensions:
1. Put the desired panel of the diaper package standing on the center of base 902 as shown in FIG. 19. Make sure the horizontal sliding plate 908 is pulled to the right so it does not touch the diaper package 320 being tested. Note: If the bag length is greater than 430 mm (e.g., double stack bags), place the bag in such a way that the artwork logo is facing/running in parallel to the vertical anchored plate to be able to measure the package width.
2. Place an 850 g weight onto the vertical sliding plate 914.
3. Allow the vertical sliding plate 914 to slide down until its bottom lightly touches desired highest point of the diaper package 320.
4. Measure the desired package dimensions in mm by reading the value that appears on the second digital meter 924 of the vertical scale.
5. Remove the weight.
6. Raise the vertical sliding plate 914 away from the diaper package 320 and remove the diaper package 320.
7. In case the diaper package 320 has more than one stack, two measurements should be taken for package width, one for each stack. The higher value should be recorded.
8. Report the determined value for each measurement to the nearest 1 mm.

The diaper package volume can be determined with standard volumetric equations such as width×height×depth. The volume of each diaper 10 in the diaper package 320 can then be calculated by dividing the volume of the diaper package 320 by the number of diapers 10 in the diaper package 320.

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of absorbent article packages comprising:
 a plurality of absorbent article packages, each of the absorbent article packages comprising a packaging material and a plurality of disposable absorbent articles disposed in the packaging material in a substantially superposed stacked configuration;
 the disposable absorbent articles each comprising a chassis including a topsheet and a backsheet and a substantially cellulose free absorbent core located between the topsheet and the backsheet and comprising absorbent particulate polymer material;
 wherein the absorbent core includes first and second absorbent layers, the first absorbent layer including a first substrate and the second absorbent layer including a second substrate;
 the absorbent particulate polymer material is deposited on the first and second substrates;
 the absorbent core further comprises thermoplastic adhesive material covering the absorbent particulate polymer material on the respective first and second substrates; and
 the first and second absorbent layers are combined together such that at least a portion of the thermoplastic adhesive material of the first absorbent layer contacts at least a portion of the thermoplastic adhesive material of the second absorbent layer, wherein the disposable absorbent article is a diaper;
 wherein the absorbent particulate polymer material is disposed between the first and second substrates in an absorbent particulate polymer material area, and the absorbent particulate polymer material is substantially continuously distributed across the absorbent particulate polymer material area;
 the absorbent particulate polymer material is deposited on the first and second substrates in respective patterns of land areas and junction areas between the land areas such that the absorbent particulate polymer material is discontinuously distributed on the first and second substrates; and
 the first and second absorbent layers are combined together such the respective patterns of absorbent particulate polymer material are offset from one another;
 wherein the width of the land areas is from about 8 mm to about 12 mm and the width of the junction areas is less than about 5 mm;
 wherein each disposable absorbent article has a longitudinal axis extending from a first end to a second end and is tri-folded substantially perpendicularly to the longitudinal axis along a first fold line and a second fold line spaced from the first fold line so as to form a central section extending from the first fold line to the second fold line, a first end section extending from the first fold line to the first end, and a second end section extending from the second fold line to the second end, so that the first section, central section, and second section are superposed to one another;
 wherein at least a first of the plurality of absorbent article packages comprises disposable absorbent articles having a first size and occupying a volume in the at least the first of the plurality of absorbent article packages of less than about 200 cc per absorbent article under base compression of from about 2500 to about 5000 N; and at least a second of the plurality of absorbent article packages comprises disposable absorbent articles having a second size different than the first size and occupying a volume in the at least the second of the plurality of absorbent article packages different than the volume occupied by the disposable absorbent articles having the first size in the first of the plurality of absorbent article packages.

2. The array of claim 1, wherein the first section, central section, and second section are substantially coextensive.

3. The array of claim 1, wherein the first section overlays the central section and the second section overlays the first section.

4. An array of absorbent article packages comprising:
 a plurality of absorbent article packages, each of the absorbent article packages comprising a packaging material and a plurality of disposable absorbent articles disposed in the packaging material in a substantially superposed stacked configuration;
 the disposable absorbent articles each comprising a chassis including a topsheet and a backsheet and a substantially cellulose free absorbent core located between the topsheet and the backsheet and comprising absorbent particulate polymer material;
 wherein each disposable absorbent article has a longitudinal axis extending from a first end to a second end and is tri-folded substantially perpendicularly to the longitudinal axis along a first fold line and a second fold line spaced from the first fold line so as to form a central section extending from the first fold line to the second fold line, a first end section extending from the first fold line to the first end, and a second end section extending from the second fold line to the second end, so that the first section, central section, and second section are superposed to one another;
 wherein at least a first of the plurality of absorbent article packages comprises disposable absorbent articles having a first size and occupying a volume in the at least the first of the plurality of absorbent article packages of less than about 200 cc per absorbent article under base compression of from about 2500 to about 5000 N;
 wherein at least a second of the plurality of absorbent article packages comprises disposable absorbent articles having a second size different than the first size and occupying a volume in the at least the second of the plurality of absorbent article packages different than the volume occupied by the disposable absorbent articles having the first size in the first of the plurality of absorbent article packages.

5. The array of claim 4, wherein the first section, central section, and second section are substantially coextensive.

6. The array of claim 4, wherein the first section overlays the central section and the second section overlays the first section.

7. The array of claim 4, wherein the absorbent core includes first and second absorbent layers, the first absorbent layer including a first substrate and the second absorbent layer including a second substrate; the absorbent particulate polymer material is deposited on the first and second substrates; the absorbent core further comprises thermoplastic adhesive material covering the absorbent particulate polymer material on the respective first and second substrates.

8. The array of claim 7, wherein the first and second absorbent layers are combined together such that at least a portion of the thermoplastic adhesive material of the first absorbent layer contacts at least a portion of the thermoplastic adhesive material of the second absorbent layer.

9. The array of claim 7, wherein the absorbent particulate polymer material is disposed between the first and second substrates in an absorbent particulate polymer material area, and the absorbent particulate polymer material is substantially continuously distributed across the absorbent particulate polymer material area; the absorbent particulate polymer material is deposited on the first and second substrates in respective patterns of land areas and junction areas between the land areas such that the absorbent particulate polymer material is discontinuously distributed on the first and second substrates; and the first and second absorbent layers are combined together such the respective patterns of absorbent particulate polymer material are offset from one another.

10. The array of claim 4, wherein the disposable absorbent article is a diaper.

* * * * *